(12) United States Patent
Shetty

(10) Patent No.: US 11,040,065 B2
(45) Date of Patent: Jun. 22, 2021

(54) HERBO-MINERAL FORMULATION FOR PREVENTION, TREATMENT AND MANAGEMENT OF RENAL DISORDERS AND METHOD OF PREPARATION THEREOF

(71) Applicant: Muniyal Ayurvedic Research Centre, Manipal (IN)

(72) Inventor: M Vijayabhanu Shetty, Manipal (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 0 days.

(21) Appl. No.: 16/234,849

(22) Filed: Dec. 28, 2018

(65) Prior Publication Data
US 2019/0134087 A1   May 9, 2019

Related U.S. Application Data

(63) Continuation of application No. 16/030,271, filed on Jul. 9, 2018.

(60) Provisional application No. 62/531,216, filed on Jul. 11, 2017.

(51) Int. Cl.
| | | |
|---|---|---|
| *A61K 35/04* | (2006.01) |
| *A61K 9/20* | (2006.01) |
| *A61K 36/882* | (2006.01) |
| *A61K 36/28* | (2006.01) |
| *A61K 36/19* | (2006.01) |
| *A61K 36/59* | (2006.01) |
| *A61K 36/15* | (2006.01) |
| *A61K 36/9066* | (2006.01) |
| *A61K 36/71* | (2006.01) |
| *A61K 36/67* | (2006.01) |
| *A61K 36/185* | (2006.01) |
| *A61K 36/23* | (2006.01) |
| *A61K 36/61* | (2006.01) |
| *A61K 36/32* | (2006.01) |
| *A61K 36/899* | (2006.01) |
| *A61K 36/9068* | (2006.01) |
| *A61K 36/54* | (2006.01) |

(52) U.S. Cl.
CPC ............... *A61K 35/04* (2013.01); *A61K 9/20* (2013.01); *A61K 9/205* (2013.01); *A61K 36/15* (2013.01); *A61K 36/185* (2013.01); *A61K 36/19* (2013.01); *A61K 36/23* (2013.01); *A61K 36/28* (2013.01); *A61K 36/32* (2013.01); *A61K 36/54* (2013.01); *A61K 36/59* (2013.01); *A61K 36/61* (2013.01); *A61K 36/67* (2013.01); *A61K 36/71* (2013.01); *A61K 36/882* (2013.01); *A61K 36/899* (2013.01); *A61K 36/9066* (2013.01); *A61K 36/9068* (2013.01)

(58) Field of Classification Search
CPC ...... A61K 35/04; A61K 36/15; A61K 36/185; A61K 36/19; A61K 36/23; A61K 36/28; A61K 36/32; A61K 36/54; A61K 36/59; A61K 36/61; A61K 36/67; A61K 36/71; A61K 36/882; A61K 36/899; A61K 36/9066; A61K 36/9068
See application file for complete search history.

(56) References Cited

PUBLICATIONS

Pole, S. Vatji Tablets from Ayurvedic Medicine. Singing Dragon: UK. pp. 315-316. (Year: 2013).*
Mandar Bhasma. Internet archive date: Feb. 10, 2012. [Retrieved from the Internet on: Apr. 17, 2020], Retrieved from: <URL: https://web.archive.org/web/20121002045907/https://www.ayurmedinfo.com/2012/07/04/mandur-bhasma-benefits-dosage-ingredients-side-effects-peparation/>. 7 pages. (Year: 2012).*
Jayakumer et el. Evidence-Based Complementary and Alternative Medicine. vol. 2013 pp. 1-16. (Year: 2013).*
Tag et al. Journal of Basic and Clinical Physiology and Pharmacology | vol. 27: Issue 1. Abstract only. Published online: Oct. 17, 2015. (Year: 2015).*
Frank, J. Guar Gum: Instability & Alternatives, Part 2. Posted on the Internet: Apr. 11, 2014. Retrieved from the Internet on: Apr. 17, 2020. Retrieved from the Internet: <URL: https://knowledge.ulprospector.com/437/guar-gum-instability-alternatives-part-2/>. (Year: 2014).*
The Government of India, Biological Diversity Act, 2002.†

\* cited by examiner
† cited by third party

*Primary Examiner* — Amy L Clark
(74) *Attorney, Agent, or Firm* — Pilloff Passino & Cosenza LLP; Sean A. Passino; Rachel K. Pilloff

(57) ABSTRACT

Disclosed herein are herbo-mineral formulations comprising a combination of various herbs and minerals. The formulation includes *Cinnamomum camphora, Acorus calamus, Saussurea lappa, Andrographis paniculate, Tinospora cordifolia, Cedrus deodara, Curcuma longa, Aconitum heterophyllum, Berberis aristata, Piper longum, Plumbago rosea, Coriandrum sativum, Emblica officinalis, Terminalia chebula, Terminalia bellerica, Piper chaba, Embelia ribes, Piper nigrum, Commiphora mukul, Saccharum officinarum, Zingiber officinalis*, shilajit and bhasmas. The formulation, having nephro-protective properties, is useful in treatment of Renal disorders.

10 Claims, 7 Drawing Sheets

Fig. 3

| | | | | |
|---|---|---|---|---|
| Group I | 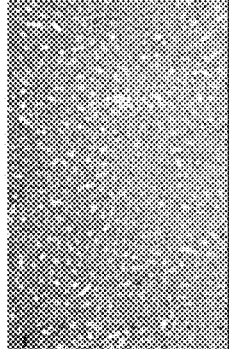 | 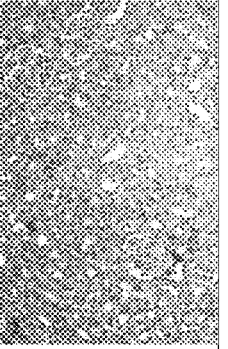 | 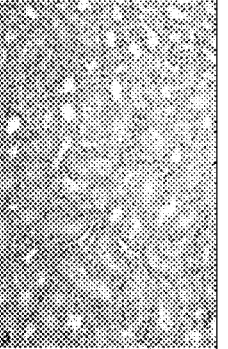 | 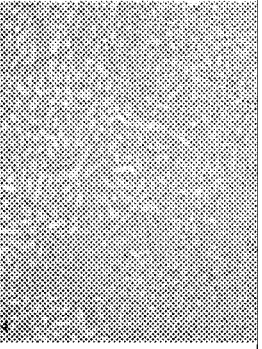 |
| | Normal parenchyma, PCT, DCT and glomeruli (H&E, X100) | Normal parenchyma, PCT, DCT and glomeruli (H&E, X200) | Inflammatory cells infiltration, minimal (H&E, X100) | Tubular dilatation, cortex, minimal (H&E, X100) |
| Group II |  |  |  | 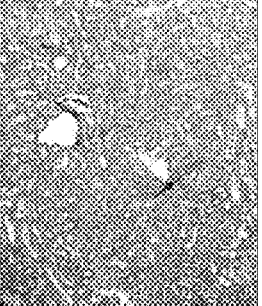 |
| | Tubular cell necrosis (black arrow), minimal; Tubular dilatation (arrow head), moderate; Tubular cell vacuolation (yellow arrow), minimal; Inflammatory cells infiltration (green arrow), moderate and Proteineous fluid in lumen (star), minimal (H&E, X400) | Tubular cell necrosis, minimal; Tubular dilatation, moderate; Tubular cell vacuolation, minimal; Inflammatory cells infiltration, moderate and Proteineous fluid in lumen, minimal (H&E, X200) | Tubular cell necrosis, minimal; Tubular dilatation, moderate; Tubular cell vacuolation, minimal; Inflammatory cells infiltration, moderate and Proteineous fluid in lumen, minimal (H&E, X100) | Inflammatory cells infiltration (arrow), glomeruli, minimal |

Fig. 4

| | | |
|---|---|---|
| Group III | 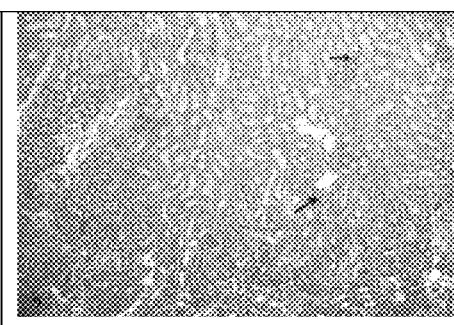 | 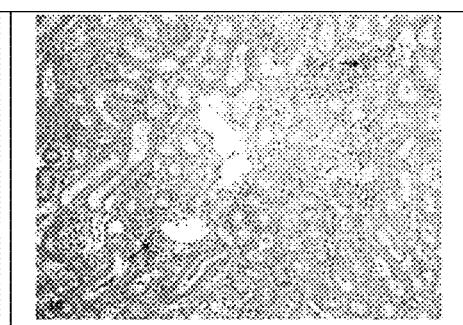 |
| | Inflammatory cells infiltration (black arrow), mild and tubular dilation (yellow arrow ), mild (H&E, X100) | Inflammatory cells infiltration (black arrow), mild and tubular dilation, mild (H&E, X200) |
| Group IV | 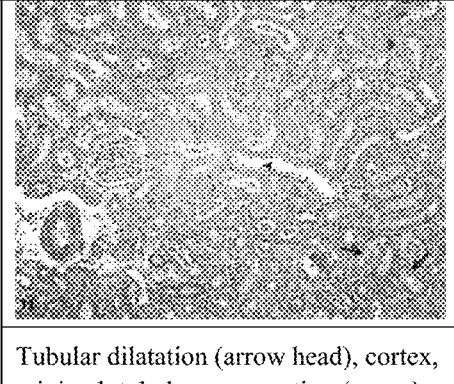 | 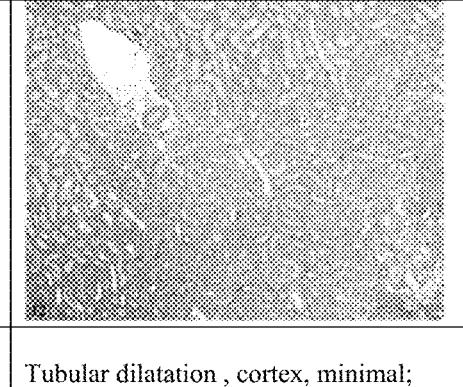 |
| | Tubular dilatation (arrow head), cortex, minimal; tubular regeneration (arrow), minimal and inflammatory cells infiltration (yellow arrow), minimal (H&E, X200) | Tubular dilatation , cortex, minimal; tubular regeneration, minimal and inflammatory cells infiltration, minimal, kidney, rat (H&E, X100) |
| | Inflammatory cells infiltration (arrow), mild and tubular dilation (arrow head), mild (H&E, X100) | Inflammatory cells infiltration,(arrow), mild and tubular dilation (arrow head), mild; kidney, rat (H&E, X200) |

Fig. 5
| Group I | Group II |
|---|---|
| 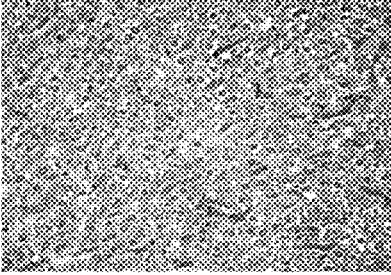 | 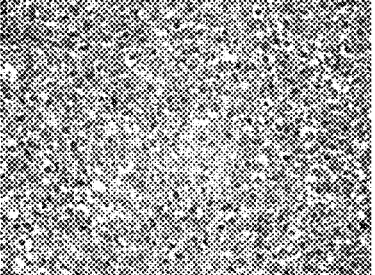 |
| Minimal degree of hepatocytes cytoplasmic vacuolation. (H&E, X400) | Marked degree of hepatocytes cytoplasmic vacuolation. (H&E, X400) |
| Group III | Group IV |
| 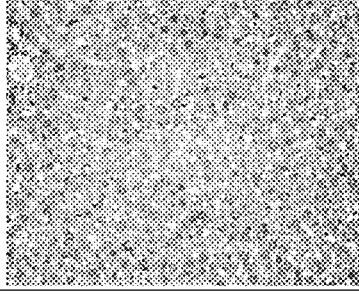 | 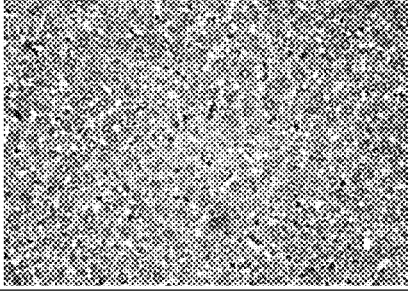 |
| Mild degree of hepatocytes cytoplasmic vacuolation. (H&E, X400) | Minimal degree of hepatocytes cytoplasmic vacuolation. (H&E, X400) |

HERBO-MINERAL FORMULATION FOR PREVENTION, TREATMENT AND MANAGEMENT OF RENAL DISORDERS AND METHOD OF PREPARATION THEREOF

CROSS REFERENCE TO RELATED APPLICATION

This application is a continuation of the U.S. application Ser. No. 16/030,271 filed on Jul. 9, 2018 which in turn claims priority of U.S. provisional application 62/531,216 filed on Jul. 11, 2017, the contents of which are incorporated herein by reference.

TECHNICAL FIELD

The embodiments disclosed in this specification relates to herbo-mineral formulations effective in the treatment, management and prevention of Renal Disorders, and more particularly as formulations that act as nephron-protective agents. It also relates to the process of preparation of such formulations.

BACKGROUND

Renal Disorders are diseases related to the Kidney function. Kidneys' ability to cleanse blood, maintain water and salt balance, and regulate volume and composition of bodily fluids, makes it one of the most important organs in the human body. Any impairment in this ability of the kidney could have grave consequences. Therefore, maintaining well-functioning kidneys is crucial for good health.

Renal disorders may be due to many reasons as in the case of Acute Kidney Injury (AKI) wherein kidney malfunction occurs due to blood loss, dehydration or use of medicines, etc. AKI is usually a more sudden and reversible condition. On the other hand, Chronic Renal Failure (CRF) is an irreversible condition with progressive loss in kidney function. One of the primary causes of CRF include Diabetes causing diabetic nephropathy. Others primary indications for kidney dysfunction include hypertension, glomerulonephritis, infection and so on.

Various methods of treating renal disorders are known. The appropriate line of treatment may be chosen based on the cause of Renal Disorder. In some cases, medication may be directed towards treating primary complications affecting the kidney function. Such medication may include medication for treating diabetes mellitus, high blood pressure, high cholesterol, anemia, etc. Further, in cases of end stage kidney disease, treatment would include dialysis and kidney transplant. Although, the symptomatic treatment regime, often implemented in the practice of allopathic medicine may help in alleviating the symptoms temporarily, they often do not focus on improving the overall health of kidneys.

The core philosophy of Ayurvedic medicine on the other hand is to attain/maintain harmony in the system and hence its approach works on improving the health of the body rather than treating symptoms. Ayurvedic interventions have also been known in treating Renal Disorders. Many herbal formulations have been developed based on the knowledge of the healing properties of various herbs. Formulations having herbs such as *Tinospora cordifolia, Terminalia chebula, Boerhavia diffusa*, etc have been developed. However, the effectiveness of such formulations is arguable. There exists a need for an effective method of treating/managing Renal Disorders.

OBJECTS OF THE DISCLOSED EMBODIMENTS

The principal object of the embodiments disclosed herein is to provide a composition and method of treating Renal disorders.

A second object of the embodiments disclosed herein is to provide a composition and method of managing Renal disorders.

Another object of the embodiments disclosed herein is to provide a composition and method of preventing Renal disorders.

Another object of the embodiments disclosed herein is to provide a herbo-mineral formulation and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which:

FIG. 1(*b*) depicts a flowchart for the preparation of Mandura Bhasma;

FIG. 1(*c*) depicts a flowchart for the preparation of Loha Bhasma;

FIG. 3 represents the histopathological observations of Kidneys of Group I (Normal control) and Group II (Positive control);

FIG. 4 represents the histopathological observations of Kidneys of Group III and Group IV treated with the embodiments disclosed herein; and FIG. 5 represents the histopathological observation of Liver of Group I, Group II, Group III and Group IV, according to the embodiments herein

DETAILED DESCRIPTION

Figure 1A:
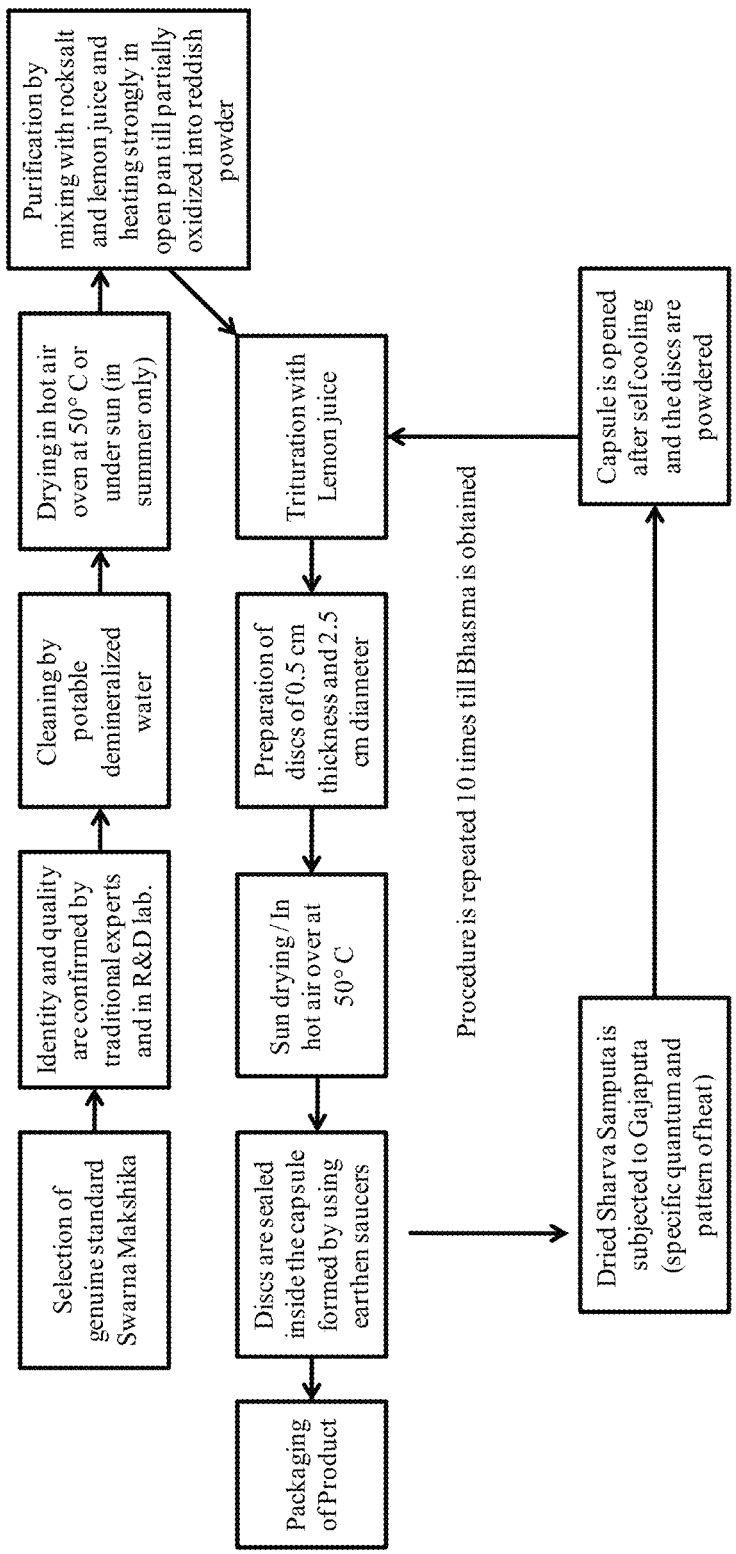
FIG. 1(*a*) depicts a flowchart for the preparation of Swarna Makshika Bhasma

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a herbo-mineral formulation of therapeutic value, and a process for the preparation of the formulation. The herbo-mineral formulation disclosed herein is useful in the treatment, prevention and management of Renal Disorders. In various embodiments herein, Renal Disorders may include any condition associated with Kidneys such as Nephritis, Nephrosis, Chronic kidney failure, etc. It has also been observed that the embodiments of the disclosed formulation may be instrumental in preventing the complications of kidney diseases such as anemia, electrolyte imbalance, high blood pressure, proteinuria, hyperkalemia, etc.

Further, the disclosed formulation also finds use in enhancing resistance of renal parenchyma against various types of nephrotoxicity. The various embodiments of the formulation also include a supplement for use as a nephroprotective agent. The formulation may be used as monotherapy or as an adjunct with other medication used to treat kidney diseases. Accordingly, the embodiments disclosed herein achieve a method for the treating/managing/preventing renal disorders.

Formulation

The disclosed embodiments herein provide herbo-mineral formulation having a combination of selected herbs and minerals. In an embodiment, the herbo-mineral formulation includes herb element and mineral element. In another embodiment, the herbo-mineral formulation includes herb element, mineral element and at least one alkali. In yet another embodiment, the herbal formulation includes herb element, mineral element, at least one alkali and at least one salt. In an embodiment, the herbo-mineral formulation may further include one or more suitable excipient.

Herb Element

In an embodiment, the herb element includes the herbs selected from a group consisting of *Cinnamomum camphora, Acorus calamus, Saussurea lappa, Andrographis paniculata, Tinospora cordifolia, Cedrus deodara, Curcuma longa, Aconitum heterophyllum, Berberis aristata, Piper longum, Plumbago rosea, Coriandrum sativum, Emblica officinalis, Terminalia chebula, Terminalia bellerica, Embelia ribes, Piper chaba, Piper longum, Saccharum officinarum, Commophora mukul, Piper nigrum* and *Zingiber officinalis* or their extracts, or the active ingredients extracted from these herbs. In another embodiment, the herb element further includes at least one of the herbs selected from *Operculina turpethum, Baliospermum montanum, Cinnamomum tamala, Cinnamomum zeylanica, Elettaria cardamomum, Bamboo manna, Boerhavia diffusa, Cyperus rotundas, Bauhinia variegate* and *Holarrhena antidysenterica*, or their extracts, or the active ingredients extracted from these herbs.

The herb element may include a specific part of the herb (also referred as herb component) such as roots, flowers, fruits, stem, bark, resin, rhizome, whole plant, extract etc. In an embodiment, the herb element may include roots of herbs selected from a group consisting of *Acorus calamus, Saussurea lappa, Aconitum heterophyllum, Berberis aristata, Piper longum, Piper chaba, Plumbago rosea, Operculina turpethum, Baliospermum montanum Elettaria cardamomum, Boerhavia diffusa* and *Cyperus rotundas*; fruits of herbs selected from a group consisting of *Coriandrum sativum, Emblica officinalis, Terminalia chebula, Terminalia bellerica, Piper longum, Embelia ribes,* and *Piper nigrum*; crystals of *Cinnamomum camphora*; heartwood of *Cedrus deodara*; leaves of *Cinnamomum tamala*; whole plant of *Andrographis paniculate*; rhizome of *Zingiber officinalis* and *Curcuma longa*; stem of *Tinospora cordifolia Saccharum officinarum* and *Piper chaba*; and stem bark of *Cinnamomum zeylanica, Bauhinia variegate* and *Holarrhena antidysenterica*; or their extract.

The herb element may also include any form of secretion, resin or discharge that may be exuded by the herb or any part of the herb. In an embodiment, the herb element may include secretion of *Bamboo manna* and oleo-gum resin of *Commophora mukul*. However, it is also within the scope of the claims provided herein for the herbo-mineral formulation to include other herb components such as leaf, flowers, etc. without otherwise deterring intended function of the herbo-mineral formulation.

The herb component maybe included in the formulation in any form that is generally known in the field. For example, the herb component may be dried, powdered, processed to form concentrates, extracts, etc. In one preferred embodiment, the herb components are dried and powdered which is further incorporated into the formulation. In another embodiment, the herb component includes stem (for example: stem of *Saccharum officinarum*) which may be crushed to yield an extract which is further used in the formulation.

In an embodiment, the herb element includes the herbs *Cinnamomum camphora, Acorus calamus, Saussurea lappa, Andrographis paniculata, Tinospora cordifolia, Cedrus deodara, Curcuma longa, Aconitum heterophyllum, Berberis aristata, Plumbago rosea, Coriandrum sativum, Emblica officinalis, Terminalia chebula, Terminalia bellerica, Piper chaba, Embelia ribes, Piper longum, Piper nigrum* and *Zingiber officinalis* in an amount in the range of 1 to 4 wt %; *Commophora mukul* in an amount in the range of 6 to 10 wt %; and *Saccharum officinarum* in an amount in the range of 2 to 6 wt %. Further, in another embodiment, the herb element includes at least one of *Operculina turpethum, Baliospermum montanum, Cinnamomum tamala, Cinnamomum zeylanica, Elettaria cardamomum, Bamboo manna, Boerhavia diffusa, Cyperus rotundas, Bauhinia variegate* and *Holarrhena antidysenterica* in an amount in the range of ≤2 wt %.

Mineral Element

In an embodiment, the mineral element includes Bhasmas or calcined preparations such as Swarna Makshika bhasma, Mandura bhasma and Loha bhasma. Alternatively, the mineral element may also be selected from a group consisting of at least one of iron rust, iron and copper pyrite. In the disclosed embodiments, the bhasmas along with the herb element form bioavailable herbo-mineral complexes which are useful in treating, preventing and managing Kidney related complications. In an embodiment, the mineral element further includes Shilajit. However, it is also within the scope of claims provided herewith for the herbo-mineral formulation to include, as a substitute or additionally, other similar calcined preparations or minerals without otherwise deterring from the intended function of the herbo-mineral formulation.

In an embodiment, the mineral element includes shilajit in the range of 6 to 10 wt %. In another embodiment, the mineral element includes Swarna Makshika Bhasma is in an amount of 1 to 4 wt %; Mandura Bhasma is in an amount of 2 to 6 wt %; Loha Bhasma is in an amount of 1 to 4 wt %.

Alkali

Further, in an embodiment, the alkali includes at least one alkali selected from a group consisting of Yavakshara and Sarjakshara. Yavakshara disclosed in the embodiments herein includes an alkali of *Hordeum vulgare*, and Sarjakshara includes Barilla. In an embodiment, the herbo-mineral formulation disclosed herein includes alkali in an amount in the range of ≤2 wt %.

Salt

In an embodiment, the salt includes at least one salt selected from a group consisting of Rock salt, Sonchal salt and Black salt. In an embodiment, the herbo-mineral formulation disclosed herein includes the salt in an amount in the range of 1 to 4 wt %.

The disclosed formulation, in the various embodiments herein, may further include a suitable excipient. The suitable excipients include solvents, binders, lubricants, herbal carriers, oils and salts that are generally known in the art. In a preferred embodiment, the excipient includes acacia gum.

Further, the amount of herb element and mineral element that may be included in the various embodiments of the disclosed formulation may be in the range of 0 to 10 wt %. In an embodiment, the formulation includes *Cinnamomum camphora* (1 to 4 wt %), *Acorus calamus* (1 to 4 wt %), *Saussurea lappa* (1 to 4 wt %), *Andrographis paniculata* (1 to 4 wt %), *Tinospora cordifolia* (1 to 4 wt %), *Cedrus deodara* (1 to 4 wt %), *Curcuma longa* (1 to 4 wt %), *Aconitum heterophyllum* (1 to 4 wt %), *Berberis aristata* (1 to 4 wt %), *Piper longum* (1 to 4 wt %), *Plumbago rosea* (1 to 4 wt %), *Coriandrum sativum* (1 to 4 wt %), *Emblica officinalis* (1 to 4 wt %), *Terminalia chebula* (1 to 4 wt %), *Terminalia bellerica* (1 to 4 wt %), *Piper chaba* (1 to 4 wt %), *Embelia ribes* (1 to 4 wt %), *Piper chaba* (1 to 4 wt %), *Piper longum* (1 to 4 wt %), *Piper nigrum* (1 to 4 wt %), *Zingiber officinalis* (1 to 4 wt %), *Commophora mukul* (6 to 10 wt %), Shilajit (6 to 10 wt %), *Saccharum officinarum* (2 to 6 wt %), Swarna Makshika bhasma (1 to 4 wt %), Mandura bhasma (2 to 6 wt %), and Loha bhasma (1 to 4 wt %).

In an embodiment, the formulation includes *Cinnamomum camphora* (1 to 4 wt %), *Acorus calamus* (1 to 4 wt %), *Saussurea lappa* (1 to 4 wt %), *Andrographis paniculata* (1 to 4 wt %), *Tinospora cordifolia* (1 to 4 wt %), *Cedrus deodara* (1 to 4 wt %), *Curcuma longa* (1 to 4 wt %), *Aconitum heterophyllum* (1 to 4 wt %), *Berberis aristata* (1 to 4 wt %), *Piper longum* (1 to 4 wt %), *Plumbago rosea* (1 to 4 wt %), *Coriandrum sativum* (1 to 4 wt %), *Emblica officinalis* (1 to 4 wt %), *Terminalia chebula* (1 to 4 wt %), *Terminalia bellerica* (1 to 4 wt %), *Piper chaba* (1 to 4 wt %), *Embelia ribes* (1 to 4 wt %), *Piper chaba* (1 to 4 wt %), *Piper longum* (1 to 4 wt %), *Piper nigrum* (1 to 4 wt %), *Zingiber officinalis* (1 to 4 wt %), *Commophora mukul* (6 to 10 wt %), Shilajit (6 to 10 wt %), *Saccharum officinarum* (2 to 6 wt %), Yavakshara, (1 to 4 wt %), Sarjakshara (1 to 4 wt %), Swarna Makshika bhasma (1 to 4 wt %), Mandura bhasma (2 to 6 wt %), and Loha bhasma (1 to 4 wt %).

Further, in yet another embodiment, the formulation includes *Cinnamomum camphora* (1 to 4 wt %), *Acorus calamus* (1 to 4 wt %), *Saussurea lappa* (1 to 4 wt %), *Andrographis paniculata* (1 to 4 wt %), *Tinospora cordifolia* (1 to 4 wt %), *Cedrus deodara* (1 to 4 wt %), *Curcuma longa* (1 to 4 wt %), *Aconitum heterophyllum* (1 to 4 wt %), *Berberis aristata* (1 to 4 wt %), *Piper longum* (1 to 4 wt %), *Plumbago rosea* (1 to 4 wt %), *Coriandrum sativum* (1 to 4 wt %), *Emblica officinalis* (1 to 4 wt %), *Terminalia chebula* (1 to 4 wt %), *Terminalia bellerica* (1 to 4 wt %), *Piper chaba* (1 to 4 wt %), *Embelia ribes* (1 to 4 wt %), *Piper chaba* (1 to 4 wt %), *Piper longum* (1 to 4 wt %), *Piper nigrum* (1 to 4 wt %), *Zingiber officinalis* (1 to 4 wt %), *Commophora mukul* (6 to 10 wt %), Shilajit (6 to 10 wt %), *Saccharum officinarum* (2 to 6 wt %), Yavakshara (1 to 4 wt %), Sarjakshara (1 to 4 wt %), Rock salt (1 to 4 wt %), Sonchal salt (1 to 4 wt %), Black salt (1 to 4 wt %), Swarna Makshika bhasma (1 to 4 wt %), Mandura bhasma (2 to 6 wt %) and Loha bhasma (1 to 4 wt %).

In another embodiment, the formulation further includes at least one of *Operculina turpethum, Baliospermum montanum, Cinnamomum tamala, Cinnamomum zeylanica, Elettaria cardamomum, Bamboo manna, Boerhavia diffusa, Cyperus rotundas, Bauhinia variegata* and *Holarrhena antidysenterica* in an amount in the range of ≤2 wt %.

Further, the amount of gum acacia may be any amount suitable to perform the activity of an excipient. In an embodiment, the formulation may include gum acacia in the range of 0 to 50 mg per 500 mg of the formulation, preferably 10 wt %.

However, it is apparent that slight variations in the amount of the ingredients may be performed without otherwise deterring from the intended function of the herbo-mineral formulation.

The herbo-mineral formulation disclosed herein may be formulated in various dosage forms such that it is suitable for oral administration. The herbo-mineral formulation may be in the form of tablets, pellets, lozenges, granules, capsules, solutions, emulsions, suspensions, or any other form suitable for use. In an embodiment, the herbo-mineral formulation is formulated in the form of tablets, preferably 500 mg tablets. For example: Table 1A depicts the quantities of each ingredient in a 500 mg tablet.

Further disclosed herein, is a tablet for treating/preventing/managing Renal disorders. In an embodiment, the tablet is a 500 mg tablet having herb element, mineral element and an excipient as depicted in Table 1A.

TABLE 1A

Each 500 mg tablet includes:

| NO. | SANSKRIT NAME | PART USED | SCIENTIFIC NAME | QUANTITY |
| --- | --- | --- | --- | --- |
| 1. | Karpura | Crystals | *Cinnamomum camphora* | 10 mg |
| 2. | Vacha | dry root | *Acorus calamus* | 10 mg |
| 3. | Kushtha | dry root | *Saussurea lappa* | 10 mg |
| 4. | Bhunimba | dry plant | *Anrographis paniculata* | 10 mg |
| 5. | Amrta | dry stem | *Tinospora cordifolia* | 10 mg |
| 6. | Devadaru | dry heartwood | *Cedrus deodara* | 10 mg |
| 7. | Haridra | dry rhizome | *Curcuma longa* | 10 mg |
| 8. | Ativisha | dry root | *Aconitum heterophylum* | 10 mg |
| 9. | Darvi | dry root | *Berberis aristata* | 10 mg |
| 10. | Pippalimula | dry root | *Piper longum* | 10 mg |
| 11. | Chitraka | dry root-pure | *Plumbago rosea* | 10 mg |
| 12. | Dhanyaka | dry fruit | *Coriandrum sativum* | 10 mg |

TABLE 1A-continued

Each 500 mg tablet includes:

| NO. | SANSKRIT NAME | PART USED | SCIENTIFIC NAME | QUANTITY |
|---|---|---|---|---|
| 13. | Amalaki | dry fruit | *Emblica officinalis* | 10 mg |
| 14. | Hareetaki | dry fruit | *Terminalia chebula* | 10 mg |
| 15. | Vibhitaki | dry fruit | *Terminalia bellerica* | 10 mg |
| 16. | Chavya | dry stem | *Piper chaba* | 10 mg |
| 17. | Vidanga | dry fruit | *Embelia ribes* | 10 mg |
| 18. | Gajapippali | dry root | *Piper chaba* | 10 mg |
| 19. | Pippali | dry fruit | *Piper longum* | 10 mg |
| 20. | Maricha | dry fruit | *Piper nigrum* | 10 mg |
| 21. | Shunthi | dry rhizome | *Zingiber officinalis* | 10 mg |
| 22. | Makshika | Incinerated ore | Incinerated Copper pyrite | 10 mg |
| 23. | Yavakshara | alkali | Alkali of *Hordeum vulgare* | 10 mg |
| 24. | Sarjakshara | alkali | Barilla | 10 mg |
| 25. | Saindhava | salt | Rock salt | 10 mg |
| 26. | Souvarchala Lavana | salt | Sonchal salt | 10 mg |
| 27. | Vida Lavana | salt | Black salt | 10 mg |
| 28. | Trivrit dry root | dry root | *Operculina terpethum* | 5 mg |
| 29. | Danti | dry root | *Baliospermum montanum* | 5 mg |
| 30. | Patraka | dry leaves | *Cinnamomum tamala* | 5 mg |
| 31. | Tvak | dry stem bark | *Cinnamomum zeylanica* | 5 mg |
| 32. | Ela | dry root | *Elettaria cardamomum* | 5 mg |
| 33. | Vamshalochana | Secretion | Bamboo manna | 5 mg |
| 34. | Punarnava | Dry root | *Boerhavia diffua* | 5 mg |
| 35. | Musta | Dry root | *Cyperus rotundas* | 5 mg |
| 36. | Kanchanara | Dry stem bark | *Bauhinia variegate* | 5 mg |
| 37. | Kutaja | Dry stem bark | *Holarrhena antidysenterica* | 5 mg |
| 38. | Sita | Extract | *Saccharum officinarum*-rock sugar | 20 mg |
| 39. | Mandura Bhasma | Incinerated iron rust | Ferri oxidum precipitatum fuscum | 20 mg |
| 40. | Loha Bhasma | Incinerated metal | Incinerated Iron | 10 mg |
| 41. | Shilajatu | fossil resin | Asphaltum | 40 mg |
| 42. | Shuddha Guggulu | oleo-gum-resin | *Commophora mukul* | 40 mg |
| 43. | Excipient | gum | Gum *acacia* | 50 mg |

Embodiments of the disclosed formulation in tablet form were analyzed for parameters including physicochemical properties such as Tablet hardness, Loss on drying, Assay, Disintegration time, Ash value, etc and the results were noted. Table 2 depicts the results of the analysis performed to determine the physicochemical properties of an embodiment of the disclosed formulation. In an embodiment, the disclosed formulation tablets have the characteristics as depicted in Table 2. It will be apparent to those skilled in the art that many modifications, both to materials and methods, may be practiced without departing from the scope of the present invention.

TABLE 2

| TEST PARAMETERS | SPECIFICATIONS |
|---|---|
| Description | Dark brown colored biconvex discs |
| Identification | Positive for Iron, Calcium |
| Average weight | 500 mg ± 12.5 mg |
| Uniformity of weight | ±2.5% of actual average weight |
| Tablet hardness | 3.6 kg/cm² |
| Loss on drying | 6.2% w/w |
| Methanol soluble extractive | 41.2% w/v |
| Chloroform soluble extractive | 12.0% w/v |
| Ash value | 15.2% w/w |
| Average Disintegration time | 26 minutes |
| Assay | Each tablet contains, Iron - 4.5 mg, Calcium - 15 mg |

Method

Disclosed herein are embodiments of a method of preparing the herbo-mineral formulation. In an embodiment, the method includes, levigating bhasmas, Guggulu and shilajit in a grinder;
adding herbs, alkali and salts into the grinder; and
adding grinding decoction, fresh juice of herbs and gomutra while continuing grinding to obtain a ground mass.

The bhasmas include at least one of Loha Bhasma, Mandura Bhasma and Swarna makshika bhasma. The mixture of bhasmas, Guggulu and Shilajit may be in semisolid form. In an embodiment, the levigation may be performed for a duration of around 3 hours.

Further, the herbs include finely powdered dried root of *Acorus calamus, Saussurea lappa, Aconitum heterophyllum, Berberis aristata, Piper longum, Piper chaba, Plumbago rosea, Operculina turpethum, Baliospermum montanum Elettaria cardamomum, Boerhavia diffusa* and *Cyperus rotundas*; finely powdered dried fruits of *Coriandrum sativum, Emblica officinalis, Terminalia chebula, Terminalia bellerica, Piper longum Embelia ribes*, and *Piper nigrum*; crystals of *Cinnamomum camphora*; finely powdered dried heartwood of *Cedrus deodara*; finely powdered dried leaves of *Cinnamomum tamala*; finely powdered dried whole plant of *Andrographis paniculata*; finely powdered dried rhizome of *Zingiber officinalis* and *Curcuma longa*; finely powdered dried stem of *Tinospora cordifolia Saccharum officinarum* and *Piper chaba*; and finely powdered dried stem bark of *Cinnamomum zeylanica, Bauhinia variegate* and *Holarrhena antidysenterica*; secretion of *Bamboo manna* and oleo-gum resin of *Commophora mukul*. In an embodiment, finely powdered herbs/herb components may be obtained by powdering and sieving the herb components through 80 mesh screen.

The grinding decoction is a decoction of herbs that may facilitate grinding. In an embodiment, the grinding decoction includes a decoction of at least one herb selected from a list consisting of: *Cyperus rotundas, Piper longum, Asparagus racemosus, Bauhinia variegate, Oldenlandia umbellata, Hemidesmus indicus, Vetiveria zizanioides, Emblica officinalis, Terminalia chebula, Terminalia bellerica* and *Boerhavia diffusa*. The decoction may be obtained by any method of decocting generally known in the field. In an embodiment, the method of preparation of grinding decoction further includes, soaking the grinding herbs i.e. powdered dry root of *Cyperus rotundas*, dried fruit of *Piper longum*, dried root of *Asparagus racemosus*, dried stem bark of *Bauhinia variegate*, dried whole plant of *Oldenlandia umbellata*, dry root of *Hemidesmus indicus*, dry root of *Vetiveria zizanioides*, dry fruit of *Emblica officinalis*, dry fruit of *Terminalia chebula*, dry fruit of *Terminalia bellerica* and dry root of *Boerhavia diffusa*; and concentrating by boiling.

In another embodiment, soaking may be performed by soaking the grinding herbs in 16 parts of water overnight. In a further embodiment, concentrating may be performed by boiling at high temperature, preferably about 80 to 85 degree Celsius, until ⅛th of the liquid remains. Concentration may be confirmed with the help of Brix meter.

Figure 2:
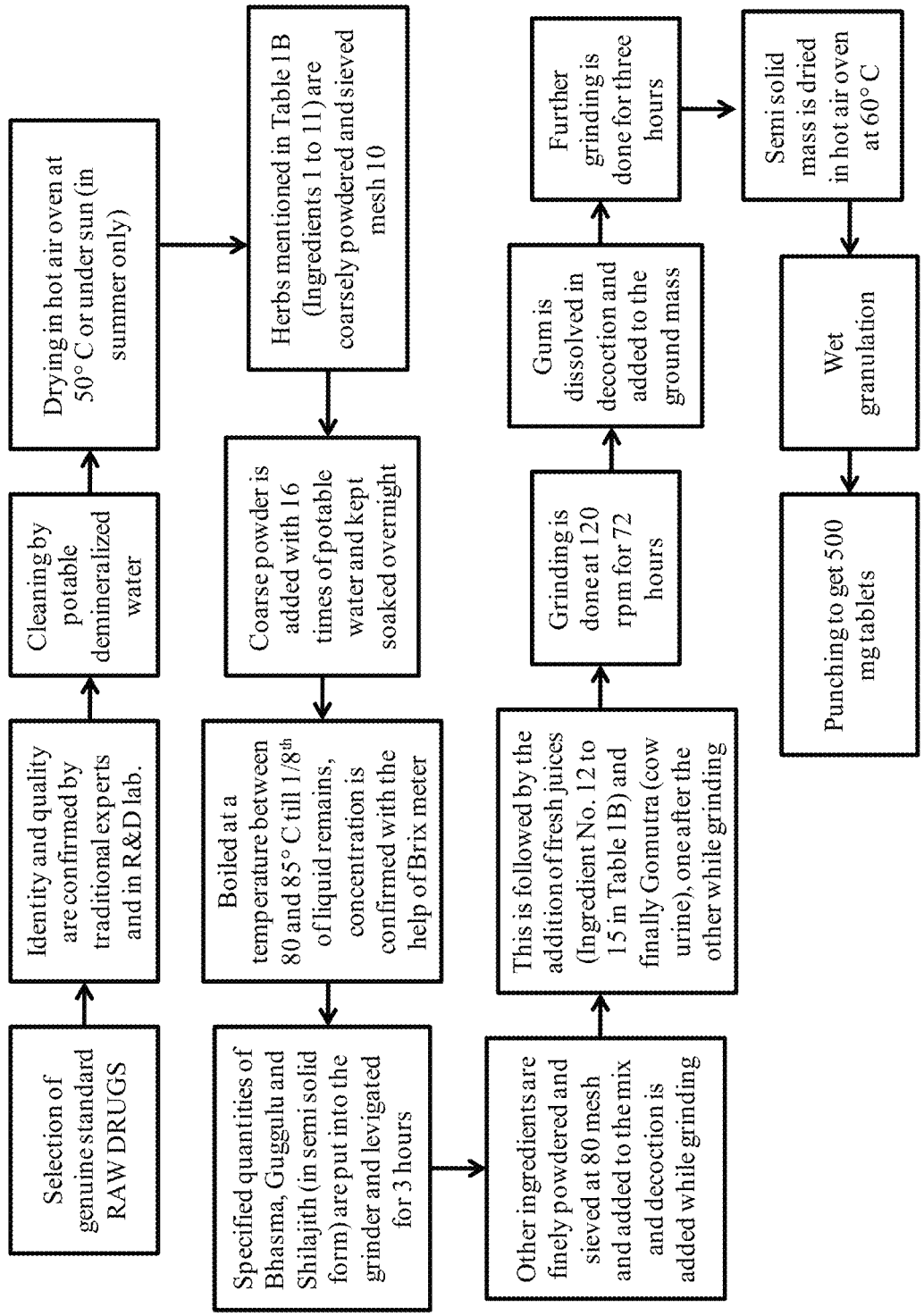
FIG. 2 depicts a flowchart for the preparation of fortified tablets.

Further, once the grinding decoction is added, fresh juice of herbs is added while continuing grinding. The fresh juice of herbs includes fresh juice of at least one of herb selected from a list consisting of *Aloe vera, Punica granatum, Cynodon dactylon* and *Ananas comosus*. The fresh juice of herbs may be added obtained by any method generally known in the field. In an embodiment, fresh juice may be obtained by grinding the herbs either together or separately. Furthermore, once the fresh juice of herbs is/are added, gomutra (cow urine) is added while grinding is continued. In an embodiment, grinding is continued for about 72 hours, preferably at 120 rpm, to obtain a ground mass. In an embodiment, the method of preparation may further include adding excipient to the ground mass, wherein gum acacia may be added to the ground mass by dissolving in the grinding decoction while continuing grinding for 3 hours to obtain a semisolid mass. The method of preparation may further include drying at 50 degree Celsius, preferably in a hot air oven, wet granulating, punching to obtain 500 mg tablets. FIG. 2 depicts a flowchart for the preparation of fortified tablets. Table 1B depicts the Herb ingredients required for grinding (grinding herbs) in one of the preferred embodiments.

TABLE 1B

List of Grinding herbs

Decoction of following herbs:

| | | | |
|---|---|---|---|
| 1. | Musta dry root | *Cyperus rotundas* | 1 part |
| 2. | Pippali dried fruit | *Piper longum* | 1 part |
| 3. | Shatavari dried root | *Asparagus racemosus* | 1 part |
| 4. | Kanchanara dried stem bark | *Bauhinia variegata* | 1 part |
| 5. | Parpata dried whole plant | *Oldanlandia umbelata* | 1 part |
| 6. | Sariva dry root | *Hemidesmus indicus* | 1 part |
| 7. | Usheera dry root | *Vetiveria zizanioides* | 1 part |
| 8. | Amalaki dry fruit | *Emblica officinalis* | 1 part |
| 9. | Hareetaki dry fruit | *Terminalia chebula* | 1 part |
| 10. | Vibhitaki dry fruit | *Terminalia bellerica* | 1 part |
| 11. | Punarnava dry root | *Boerhavia diffusa* | 1 part |
| 12. | Jala | Water | 176 parts |
| 13. | | Avashesha (Reduced to) | ⅛ part of water |

TABLE 1B-continued

List of Grinding herbs

Fresh juice of following herbs:

| | | | |
|---|---|---|---|
| 14. | Kumari fresh juice | *Aloe vera* | 1 part |
| 15. | Dadima fresh juice | *Punica granatum* | 1 part |
| 16. | Durva fresh juice | *Cynodon dactylon* | 1 part |
| 17. | Ananasa frsh fruit juice | *Ananas comosus* | 1 part |
| 18. | Gomutra | Cow urine | 1 part |

The bhasmas that are used in the various embodiments of the disclosed herbo-mineral formulation may be prepared by methods that are generally known in the field. Bhasmas may be prepared by selecting genuine standard minerals as starting material such as Iron rust, Iron, copper pyrite etc; drying in a hot air oven; purifying the mineral by triturating, quenching, boiling etc; triturating with herbal decoction; preparing into discs; drying of discs; preparing sharavasam puta, subjecting Sharavasam puta to Gaja puta, and powdering of discs once cooled. In an embodiment, the method is repeated 30 times till bhasma is obtained.

Figure 1B:
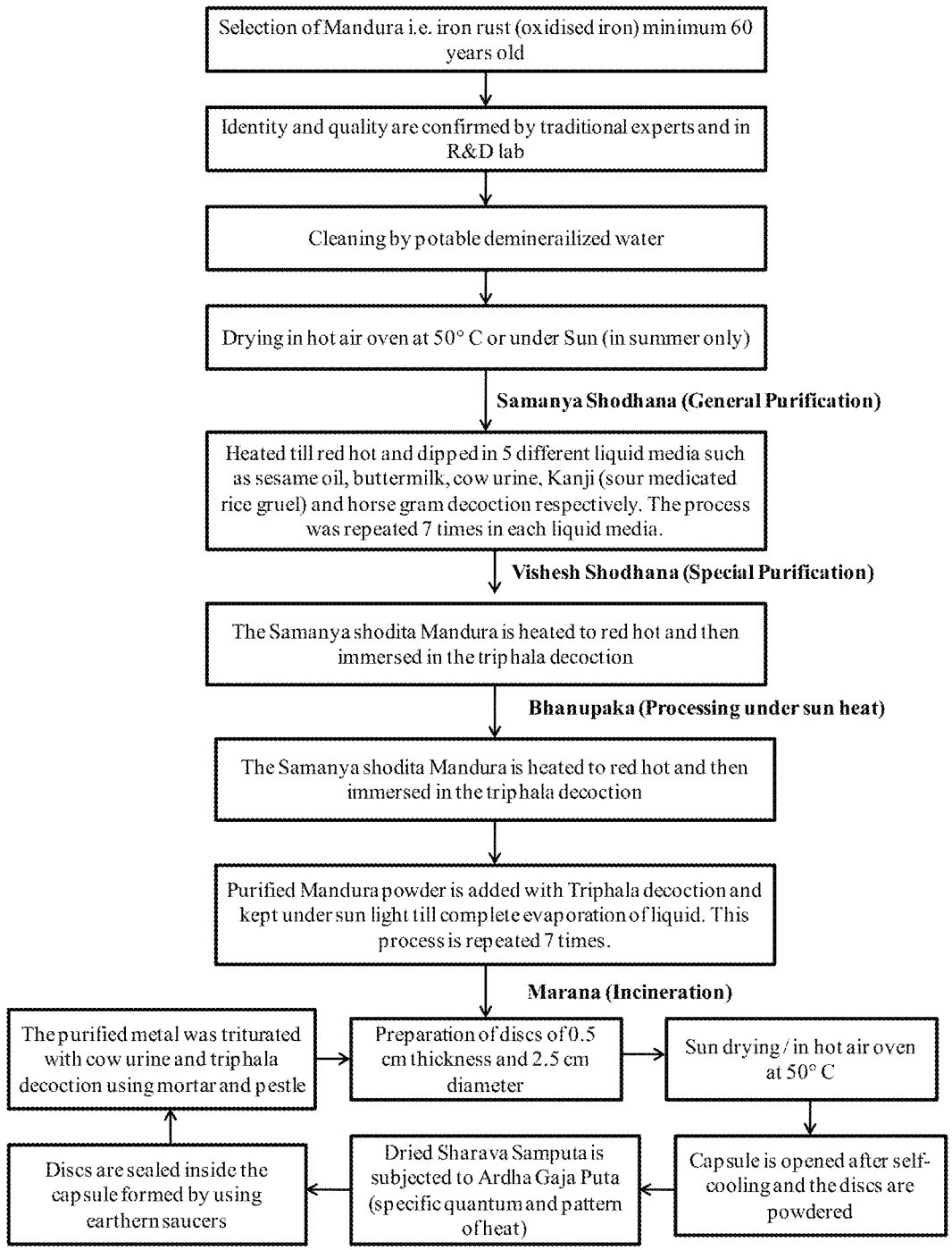
Figure 1C:
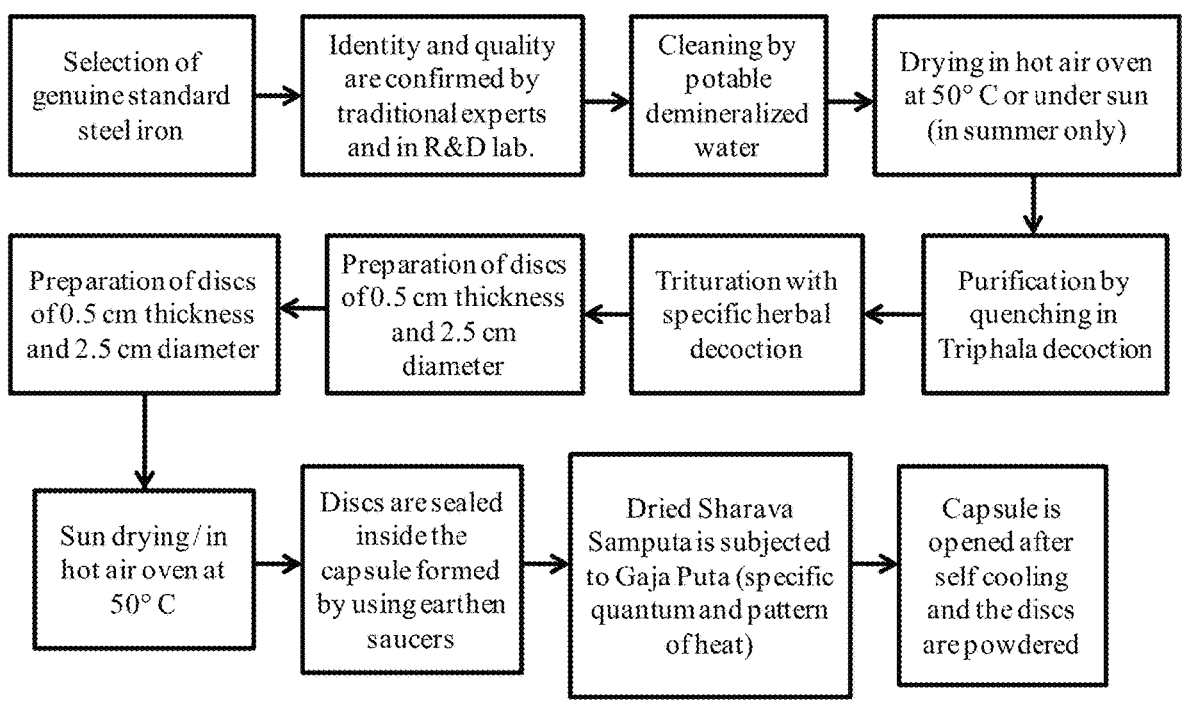

The starting materials used in the preparation of bhasmas may include standard minerals generally used in the field. In an embodiment, the preparation of Swarna makshika Bhasma includes Swarna makshika as the starting material. FIG. 1(*a*) depicts a flowchart for the preparation of Swarna Makshika Bhasma using Swarna makshika as the starting material. In another embodiment, the preparation of Mandura Bhasma includes Iron rust as the starting material. FIG. 1(*b*) depicts a flowchart for the preparation of Mandura Bhasma using Iron rust as the starting material. In an embodiment, the preparation of Loha Bhasma includes steel iron as the starting material. FIG. 1(*c*) depicts a flowchart for the preparation of Loha Bhasma using steel iron as the starting material.

The purification, or shodhana, of the mineral may be performed by generally known methods in the field. In an embodiment, the purification may be by mixing the starting material with rock salt and lemon juice wherein it is further used in the preparation of Swarna makshika Bhasma. In an embodiment, the purification may be by heating the mineral till red hot and dipping in 5 different liquid media such as sesame oil, butter milk, cow urine, Kanji (sour medicated rice gruel) and Horse gram decoction wherein it is further used in the preparation of Mandura Bhasma. In another embodiment, the purification may be by quenching the mineral in Triphala decoction which is further used in the preparation of Loha Bhasma.

The herbal decoction/juices used for triturating may be any herbal decoction/juice that is generally used for triturating in the preparation of bhasmas. For example, the herbal decoction/juice may include triphala, lemon juice, Gomutra (cow's urine) etc. In an embodiment, the herbal decoction includes cow urine and triphala decoction wherein it is useful in the preparation of Mandura bhasma. In another embodiment, the herbal decoction specifically includes Triphala Kashaya (decoction of fruits of *Terminalia chebula, Terminalia bellerica* and *Emblica officinalis*) wherein it is useful in the preparation of Loha Bhasma. In yet another embodiment, trituration may be performed with lemon juice wherein it is useful in the preparation of Swarna makshika bhasma.

Treatment

Disclosed herein are embodiments of the method of treating/preventing/managing Renal disorders and associated complications. The embodiments disclosed herein are also instrumental in preventing the complications associated with kidney diseases such as anemia, electrolyte imbalance, high blood pressure, proteinuria, hyperkalemia, etc.

In an embodiment, the method includes administering to a patient a composition as described in any of the embodiments disclosed herein. In an embodiment, the patient may include any individual in need of such treatment including ones having/suspected of having Renal disorders or its symptoms. Further, the patient may also include any individual having/suspected of having complications associated with Renal disorders such as anemia, electrolyte imbalance, high blood pressure, proteinuria, etc.

In a preferred embodiment, the method includes administering to a patient a composition having herb element, mineral element, at least one alkali, at least one salt and suitable excipient, wherein the herb element includes *Cinnamomum camphora* (1 to 4 wt %), *Acorus calamus* (1 to 4 wt %), *Saussurea lappa* (1 to 4 wt %), *Andrographis paniculata* (1 to 4 wt %), *Tinospora cordifolia* (1 to 4 wt %), *Cedrus deodara* (1 to 4 wt %), *Curcuma longa* (1 to 4 wt %), *Aconitum heterophyllum* (1 to 4 wt %), *Berberis aristata* (1 to 4 wt %), *Piper longum* (1 to 4 wt %), *Plumbago rosea* (1 to 4 wt %), *Coriandrum sativum* (1 to 4 wt %), *Emblica officinalis* (1 to 4 wt %), *Terminalia chebula* (1 to 4 wt %), *Terminalia bellerica* (1 to 4 wt %), *Piper chaba* (1 to 4 wt %), *Embelia ribes* (1 to 4 wt %), *Piper chaba* (1 to 4 wt %), *Piper longum* (1 to 4 wt %), *Piper nigrum* (1 to 4 wt %), *Zingiber officinalis* (1 to 4 wt %), *Commophora mukul* (6 to 10 wt %), *Saccharum officinarum* (2 to 6 wt), and/or at least one of herb selected from *Operculina turpethum, Baliospermum montanum, Cinnamomum tamala, Cinnamomum zeylanica, Elettaria cardamomum, Bamboo manna, Boerhavia diffusa, Cyperus rotundas, Bauhinia variegata* and *Holarrhena antidysenterica*, ($\leq 2$ wt %); the mineral element includes Shilajit (6 to 10 wt %) and at least one of bhasma selected from Mandura bhasma (2 to 6 wt %) and Loha bhasma (1 to 4 wt %); at least one alkali selected from a group consisting of Yavakshara ($\leq 2$ wt %) and Sarjakshara ($\leq 2$ wt %); and at least one salt selected from a group consisting of Rock salt (1 to 4 wt %), Sonchal salt (1 to 4 wt %) and Black salt (1 to 4 wt %).

In an embodiment, the disclosed formulation may be used such that it acts as at least one of anti-lipid, free radical scavenging, hypolipidemic and nephro-protective agent.

The disclosed method of treatment may be used as a primary line of treatment or as an adjunct to other treatment methods for kidney disorders.

The patient may be administered a therapeutically effective amount of the embodiments of the disclosed formulation. The therapeutically effective amount may vary depending on the patient. In an embodiment, the therapeutically effective amount is 500 to 1000 mg administered one to three times a day.

Embodiments of the disclosed formulation were subjected to acute oral toxicity study, and a study to check its effect on behaviour and nervous system. The studies showed that the embodiments of the formulation are free from toxicity even at a dose of 6000 mg/kg weight which was the maximum possible dose. It was also found to have no harmful effects on behavioural and nervous system.

Embodiments of the Disclosed formulation (also referred as Test product or Test drug) were further evaluated for efficacy of nephron-protective activity by preclinical and clinical studies, as described hereunder by way of examples. Embodiments are further described by reference to the following examples by way of illustration only and should not be construed to limit the scope of the claims provided herewith. It will be apparent to those skilled in the art that many modifications, both to materials and methods, may be practiced without departing from the scope of the claims.

Example 1: Preclinical Study

The aim of this study was to analyze the effect of Test drug against Gentamicin induced Nephrotoxicity in male Sprague dawley rats.

Experiment Details:

24 Sprague dawley rats between the range of 200-300 g were selected and acclimatized for a period of 5 days to the laboratory condition. After acclimatization, animals were randomized into four groups (Group I-IV) consisting of six animals per group. Group I and II animals received vehicle (0.5% CMC); group III and IV received Test drug at 100 and 200 mg/kg b.wt., p.o., respectively for a period of 14 days. After 1 hr of drug administration, all experimental animals received Gentamicin (100 mg/kg; i.p) intraperitoneally once daily except those from normal control group for 14 days. Weekly drug dosage was adjusted based on the respective week body weight of animals.

Clinical signs of toxicity, morbidity and mortality were observed daily till the day of necropsy. Body weight was recorded once before dosing and on day 7 and 14. Urine output and Urine biochemistry was analyzed on day 7 and 14 by individually housing the animals in metabolic cages. Biochemistry and electrolytes in serum were also analyzed at the end of treatment and necropsy. A renal weight change and gross pathology of liver and renal tissues were observed.

Treatment related death and clinical signs of toxicity were not found between the experimental animals. Significant decrease in body weight was observed on day 14 in Group II. Group III and Group IV animals prevented loss of body weight in comparison with Group II.

No change in color, pH, and Specific gravity, excretion of blood, nitrites, bilirubin, and ketones in urine were noted between Group I, Group II, III and IV animals. Traces of glucose, micro albumin, protein, albumin, urobilinogen and leucocytes were observed in urine of group II, III and IV at day 14.

Group II animals also showed significant elevation in urea, creatinine, uric acid, alkaline phosphatase, gamma glutamyl transferase were observed at day 14 in urine and blood when compared to Group I. Group III and IV (Test drug, 100 and 200 mg/kg) significantly attenuates these levels a dose dependent manner.

No significant change in serum electrolytes such as potassium, pH, sodium was observed between the treated groups when compared to Group I. Significant elevation in Calcium was observed in Group II which was significantly attenuated by Group IV to normal range.

Lipid peroxidation was significantly ($p<0.05$) augmented by gentamicin administration with concomitant decrease in antioxidants, Super oxide dismutase, reduced Glutathione and Glutathione peroxidase in Group II. Group III and IV animals reverse these alterations in a dose dependent manner.

Gentamycin has not shown any gross pathological changes between the groups. However, histopathology of renal tissues reveal mild to moderate degree of lesions such as tubular degeneration, tubular cell necrosis etc, in Group II animals which confirms the induction of nephrotoxicity in rats. Remarkable decrease in severity and incidence of lesions in renal tissues was observed in Group IV animals (Test drug treated at 200 mg/kg b.wt) when compared to animals of Gentamycin treated group and concurrent control.

Histology of Livers of animals treated with Test drug treated at 100 and 200 mg/kg b.wt reveals decrease in severity of inflammation in group II animals.

Altogether, the present study reports the potential nephrotoxicity produced by Gentamicin in rats through the excretion of glucose, protein, micro albumin, leucocytes and urobilinogen in urine. Test drug treatment has exasperated to counteract these responses at both dose levels with antioxidants defense. The result of this study demonstrated that Test drug has potent nephroprotective action upon Gentamycin-induced renal damage in rats and possessed antilipid peroxidative and free radical scavenging activities.

Experiment Details:

Materials:

| | |
|---|---|
| Species/Strain | Rat/Sprague Dawley |
| Sex | Male |
| Body weight at the time of Dosing | 200-260 g |
| Acclimatization | Minimum five days under laboratory conditions. |

Chemicals Used:

| | |
|---|---|
| Gentamicin | Tris Hcl Buffer (pH 7.2) |
| Anaesthetic ether | Sodium pyrophosphate buffer (0.025M) |
| Tri Chloro acetic acid | NADH (780 µM) |
| Phosphate buffer (pH:8) | Saline |
| Dithio dinitro benzoic acid (DTNB) in 0.2M | Standard malondialdehyde |
| Phenazonium Metho Sulphate (PMS) (186 µM) | Sodium azide |
| Nitro Blue Tetrazolium chloride (NBT) (300 µM) | Hydrogen Peroxide |
| Reduced glutathione | Glacial acetic acid |
| Thiobarbituric acid (0.8%, TBA) in 0.5N HCl. | n-butanol |
| Butylated Hydroxyl Toluene (BHT) 0.05% in methanol. | Potassium•EDTA |

Consumables

| | |
|---|---|
| Surgicals | Rat Cages with grid |
| Micro Tips-10 µl & 1000 µl | Husk |
| Eppendrof vial | 2 ml Syringes |
| Capillaries (heparinised) | Oral gavage |
| Polypropylene water bottle | |

Instrument/Equipment Used:
Below mentioned equipment's were periodically calibrated as applicable;

| | |
|---|---|
| Anaesthetic chamber | Semi automated analyser |
| Animal weighing Balance | Fully automated analyser |
| Analytical weighing balance | Microplate reader |
| Metabolic cage | Micropipette - 100-1000 µl, 20-200 µl |
| Tissue homogenizer | Refrigerated centrifuge |
| Cyclomixer | Electrolyte analyser |

Experimental Conditions:

| | |
|---|---|
| Environmental conditions | Temperature, humidity and air exchange were maintained in the range of 19-23° C., 30-70% and 12-15 air changes per hour respectively. The animals were provided with photoperiod of 12 hours artificial light and 12 hours dark. |
| Housing | Animals were housed in groups polypropylene cages with deducted and bedding material |
| Diet & Water | Animals were provided with commercially available laboratory rodent feed and reverse osmosis water. |

Procedure:

Grouping and Dosing: Animals were grouped six per cage in the following manner. Table 3 depicts the grouping and dosing of animal.

TABLE 3

| Group | Treatment | Total animals |
|---|---|---|
| I Normal Control | 0.5% CMC | 6 |
| II Positive Control | Gentamicin (100 mg/kg/day in i.p) + 0.5% CMC | 6 |
| III Test drug | Test drug (100 mg/kg, p.o) + Gentamicin (100 mg/kg/day in i.p) | 6 |
| IV Test drug | Test drug (200 mg/kg, p.o) + Gentamicin (100 mg/kg/day in i.p | 6 |

Induction: All experimental animals received Gentamicin (100 mg/kg; i.p) except normal control 1 hr after the drug treatment for 14 days.

Dose Formulation: The test and reference drug was freshly prepared with appropriate volume of 0.5% CMC prior to administration.

Dosage:

10 ml/kg were the dose volume

Dosage of administration of test substance was adjusted based on the weekly body weight.

Test drug, reference drug, vehicle formulations were administered orally to respective animals via intragastric tube for a period of 14 days.

Urine Collection:

On day 7 and 14, animal will be housed for 24 hr in metabolic cages for urine collection.

Urine output was measured and used for analysis using urine strip.

Blood Collection:

On day 15, animals were anesthetized using Isoflurane for blood collection. Blood was collected in an Eppendorf vials and kept in slanting position at room temperature for 15-30 minutes for serum separation.

Vials were centrifuged at 3500 rpm for 10 minutes for separation and used for Biochemical analysis.

Histopathology:

Organ kidney and liver were collected for histopathological process

Data Analysis: All values were expressed individually as Mean±S.E.M. Statistical analyses were performed on the different conditions using one-way ANOVA (F value), followed by the post-hoc analysis (Tukey multiple comparison test). $p<0.05$ and $p<0.01$ are considered as statistically significant.

Observation:

Mortality & Morbidity: Mortality and morbidity of the animals was checked daily.

Clinical Signs: Clinical signs were observed in experimental animals throughout the study.

Body Weight: Body weight was recorded on day 0, 7 and 14.

Urine parameters: pH, specific gravity, Bilirubin, blood, nitrites, glucose, microalbuminuria (MALB), Albumin, protein, ketones and leucocytes in urine were quantified using urine analyser via urinary dip strips. Urea, Creatinine, Uric acid and Albumin content and the activity of enzymes such as alkaline phosphatase (ALP), gamma glutamyl transferase (GGT) and acid phosphatase (ACP) in urine was analyzed using Bio-Systems Diagnostics Pvt. Ltd with Semi Automated biochemical analyser.

Blood parameters: Serum electrolytes (Calcium, Potassium, pH, sodium) were analyzed using Cornley Acculyte 5P electrolyte analyzer. Blood urea nitrogen (BUN), Creatinine, uric acid, total protein, albumin, globulin, alkaline phosphatase (ALP), gamma glutamyl transferase (GGT) and acid phosphatase (ACP) activities were analyzed using Bio-Systems Diagnostics Pvt. Ltd as per kit manual.

Oxidative stress markers: About 500 mg of renal tissues were homogenized in 5 mL KCl [10 mM] phosphate buffer (1.15%) with ethylene-diamine tetra acetic acid (EDTA, pH 7.4) and centrifuged at 5,000 rpm for 60 min. The supernatant was used to measure oxidative stress markers such as superoxide dismutase (SOD), catalase (CAT), reduced glutathione (GSH), lipid peroxides (TBARS), and total protein (TP) using Multi plate reader.

Tissue Lipid Peroxide (LPO, TBARS) Level: Tissue lipid peroxide (LPO) level was determined as TBA-reactive substances according to the method of Ohkawa et al (1979). To 1.0 ml of homogenate, 3.0 ml of 0.8%, TBA HCl reagent and 0.5 ml of Butylated Hydroxyl Toluene (BHT) 0.05% in methanol were added and mixed thoroughly. The mixture was kept in a boiling water bath for 15 minutes. After cooling, the tubes were centrifuged at 1000 g for 10 minutes and the supernatant was taken for the measurement. A standard solution of malondialdehyde at various concentrations was treated in a similar manner. The absorbance of pink chromophore was read at 535 nm against a reagent blank. Values were expressed as microgram/gm tissue.

Total protein: Protein content in tissue was measured by Lowry et al., 1951. To 0.025 ml of homogenate, 0.5 ml of Lowry reagent was added and mixed thoroughly. The mixture was kept at room temperature for 15 minutes. A standard solution of BSA at various concentrations was treated in a similar manner. The absorbance of blue chromophore was read at 540 nm against a reagent blank. Values were used to express the enzyme activity Enzymic and Non-Enzymic Antioxidants Superoxide Dismutase: Superoxide dismutase activity was assayed by the method of Kakkar et al., 1984. Superoxide dismutase was assayed by taking 0.05 ml of homogenate followed by addition of 0.3 ml of sodium pyrophosphate buffer, 0.025 ml of Phenazonium Metho Sulphate (PMS; 186 µM) and 0.075 ml of Nitro Blue Tetrazolium chloride (NBT, 300 µM). The reaction was started by addition of 0.075 ml of NADH (780 µM). After incubation at 300 C for 90 seconds, the reaction was stopped by addition of 0.25 ml glacial acetic acid. Then the reaction mixture was stirred vigorously and shaken with 2.0 ml of n-butanol. The mixture was allowed to stand for 10 minutes and centrifuged. 1.5 ml of n-butanol alone was served as blank. The colour intensity of the chromogen was read at 560 nm.

Calculation: Enzyme activity (1 Unit)=50% inhibition/minute.

Glutathione Peroxidase: Glutathione peroxidase activity was estimated by the method of Rotruck et al., (1973). Activity of Glutathione peroxidase (GPx) was assayed by taking 200 µl of 0.4 mM Tris HCl Buffer (pH 7.2), 200 µl K.EDTA (0.4 mM) along with 100 µl of sodium azide (10 mM) and 200 µl of enzyme preparation and mixed well. Thereafter, 200 µl of reduced glutathione solution (2 mM) followed by 0.1 ml $H_2O_2$ were added. The overall reaction was arrested by adding 0.5 ml of 10% TCA. The non-enzymatic reaction rate was correspondingly assessed by replacing the enzyme sample by buffer. The precipitate was removed by centrifugation at 4000 rpm for 10 minutes. The remaining reduced glutathione in the supernatant was determined by adding 1.0 ml of 0.6 mM Dithio dinitro benzoic acid (DTNB) in 0.2 M Phosphate buffer (pH 8.0). The absorbance was read at 412 nm using an UV/Visible spectrophotometer. The content of GSH was calculated using standard graph of GSH. The results are expressed in microgram of GSH consumed per minute per mg protein.

Catalase: Catalase activity was estimated by the method of Sinha AK 1972. Two set of tubes were arranged and labelled as Test and Control. To 'Test', 0.1 ml of homogenate and 0.5 ml of Phosphate buffer was added and the reaction was initiated by adding 0.4 ml of H2O2. To Control, 0.6 ml of Phosphate buffer and 0.4 ml of $H_2O_2$ were added. The reaction mixture was incubated at 5 minutes at room temperature. After incubation, 2 ml of Dichromatic acetic acid was added and boiled for 10 minutes. 0.1 ml of homogenate was added to control tubes. The chromic acetate thus produced is measured colorimetrically at 570 nm. The activity of CAT was expressed as units/mg protein. One unit of CAT activity represents the amount of enzyme that destroys 1 µmole H2O2/min.

Reduced Glutathione (GSH): Reduced glutathione content was measured by the method of Moren et al., 1979. 0.25 ml of homogenate was added to equal volume of ice cold 5% TCA to precipitate the protein present in the tissue. The precipitate was removed by centrifugation at 4000 rpm for 10 minutes. To 1 ml aliquot of supernatant, 0.25 ml of phosphate buffer, pH 8.0 and 0.5 ml of 0.6 mM Dithio dinitro benzoic acid (DTNB) in 0.2 M Phosphate buffer (pH 8.0). was added and mixed well. The absorbance was read at 412 nm using an UV/Visible spectrophotometer. The content of GSH was calculated using standard graph of GSH. The results are expressed in micromoles of GSH per gram tissue.

Necropsy: At the end of the study, all surviving animals were euthanized by CO2 asphyxiation and all animals were subjected to detailed gross necropsy which includes external surface of the body and gross examination of external orifices, the cranial, thoracic and abdominal cavities and their contents.

Histopathology: From the collected organs, adequate amount of kidney and liver tissues were placed in formalin filled container (1:10 ratio) for fixation, approx 3-5 mm thick tissues were trimmed, processed in alcohol, xylene and impregnate in paraffin. Processed tissues were embedded in paraffin block, sectioned at 3-5 micron and stained with H & E for Histopathology examination.

The following grading system was used for histopathology evaluation in the study:
1—Minimal
2—Mild
3—Moderate
4—Marked
5—Severe Results and Discussion:

Mortality & Morbidity: No morbidity or mortality was observed in experimental animals throughout the study.

Clinical Signs: No abnormal clinical signs were observed in experimental animals throughout the study. All the animals were found normal.

Body Weight: Significant body weight change was not observed on day 7 between the control and treatment groups. However, significant ($p<0.05$) decrease in body weight was observed in Group II on day 14 when compared to Group I. Though slight increase in body weight was observed in Test drug treated rats (Group III and IV), were insignificant and not comparable to normal control (Group I). Table 4 depicts the effect of Test drug on Body Weight Changes in Nephrotoxicity Induced Rats Urine parameters: Urinalysis (UA) is used as a screening tool to detect substances or cellular material in the urine associated with renal dysfunction or urinary tract infections (UTI). Significant increase in urine output was noted at day 7 and 14 of group II animals when compared to group I. But there was no significant change in urine output was noted at day 7 and day 14 of group IV when compared to group II. Table 5 depicts the effect of Test drug Treatment on Urine Output In Nephrotoxicity Induced Rats.

No change in color, pH and Specific gravity between control and treated animals. There were no excretion of blood, nitrites, bilirubin, ketones were noted in control and treated animals.

Trace amount of glucose (5.6 mmol/L), micro albumin, protein, significant ($p<0.01$) level of albumin, urobilinogen and leucocytes were observed in urine of group II, III and IV at day 14 and no such elimination was noted in Group I. The result shows that gentamicin induction causes slight damage in renal tissues which in turn reflects the excretion of Glucose, protein, micro albumin, leucocytes and urobilinogen. This may be due to the increased renal tubular secretion, increased glomerular filtration, obstruction in the urinary tract and reduced glucose reabsorption in renal tubular disease. Test drug treatment has counteracted these responses which was insignificant. Table 6 depicts the effect of Test drug Treatment on Urinary Parameters In Nephrotoxicity Induced Rats.

On the other hand, significant elevation in urea, creatinine, uric acid, alkaline phosphatase (ALP), gamma glutamyl transferase (GGT) were observed at day 14 in Group II animals when compared to Group I. Test drug at two dose levels significantly attenuates these levels when compared Group II. Table 7 depicts the effect of Test drug Treatment on Urine Biochemistry in Nephrotoxicity Induced Rats. Table 8 depicts the effect of Test drug Treatment on Organ Weight in Nephrotoxicity Induced Rats Blood parameters: Significant elevation in blood urea nitrogen (BUN), Creatinine, uric acid, alkaline phosphatase (ALP), gamma glutamyl transferase (GGT) were observed in Group II animals when compared to Group I. Group III and IV (Test drug at two dose levels) attenuates GGT and uric acid levels significantly when compared with group II and also reduced the urea and creatinine, the levels were insignificant. Table 9 depicts the effect of Test drug Treatment on Blood Biochemistry In Nephrotoxicity Induced Rats.

No significant change in serum electrolytes such as potassium, pH, sodium were observed between the treated groups. Significant elevation in Calcium was observed in Group II which was significantly attenuated to normal by Test drug high dose treatment. As reported earlier, calcium had a relation with Gentamycin. It impairs calcium transport in the renal tubules (Arphitha et al 2008) and increases the calcium level in serum. Table 10 depicts the Effect of Test drug Treatment on Serum Electrolytes in Nephrotoxicity Induced Rats Oxidative stress markers: Lipid peroxidation in the renal tissues is assessed by the accumulation of MDA, was significantly ($p<0.05$) augmented by gentamicin administration with concomitant decrease in antioxidants, Super oxide dismutase, reduced Glutathione and Glutathione peroxidase Test drug treatment significantly maintained the lipid peroxidation ($p<0.05$) and glutathione ($p<0.01$) in gentamycin induced rats nearer to normal. Similarly, Test drug treatment dose dependent manner amplified the super oxide dismutase and glutathione peroxidase levels which were not significant. Table 11 depicts the effect of Test drug Treatment on Renal Stress Marker In Nephrotoxicity Induced Rats Gross Pathology: During necropsy, gross lesions like discoloration, pale, pitted surface, bilateral, was observed in kidneys of Group II animals. Any gross lesions were not noticed in other organs in any of the study animals.

Histopathology: Kidneys of control animals treated with vehicle alone revealed tubular degeneration and or regeneration, tubular dilatation, and inflammatory cells infiltration but only at within normal limit to minimal severity. Kidneys of Gentamycin (100 mg/kg body weight) induced animals revealed classical nephrotoxicity induced histopathological lesions viz., tubular degeneration and/or regeneration, tubular dilatation, tubular cell vacuolation, tubular cell necrosis and inflammatory cells infiltration with higher severity ranging from mild to moderate degree. Table 12 depicts the Individual Animal Histopathological Findings.

Animals from both groups treated with Test drug did show protective effect against gentamycin induced toxicity. However, remarkable effect i.e. decreases in severity and incidence of lesions in the kidneys of animals was observed in Test drug treated at 200 mg/kg b.wt. compared to animals treated with Test drug (100 mg/kg b.wt.). Table 13 depicts the Summary of Grading System for Histopathology Evaluation of Kidney Histopathology of liver though not remarkable but revealed inflammatory cells infiltration with minimal severity in 3/6 animals from gentamycin treatment group which also appeared to be decrease to 1/6 animals treated with Test drug at 200 mg/kg b.wt. Table 14 depicts the Summary of Grading System for Histopathology Evaluation of Liver.

FIG. 3 represents the histopathological observations of Kidneys of Group I and Group II. FIG. 4 represents the histopathological observations of Kidneys of Group III and Group IV. FIG. 5 represents the histopathological observation of Liver OF Group I, Group II, Group III and Group IV.

All other histopathological findings were either spontaneous and or background changes, related to agonal changes, routinely observed in rats of this age.

Tabulation of Results is as follows:
Table 4: Effect of Test drug on Body Weight Changes in Nephrotoxicity Induced Rats

| Treatment | Animal No | Body weight (g) | | |
|---|---|---|---|---|
| | | Day 0 | Day 7 | Day 14 |
| Normal control | 1 | 257 | 284 | 242 |
| 0.5% CMC | 2 | 238 | 257 | 234 |
| | 3 | 269 | 300 | 247 |
| | 4 | 238 | 269 | 252 |
| | 5 | 242 | 216 | 210 |
| | 6 | 244 | 271 | 251 |
| Mean ± SEM | | 243.00 ± 7.92 | 266.16 ± 11.68 | 239.33 ± 6.45 |
| Gentamicin | 7 | 230 | 184 | 156 |
| (100 mg/kg)i.p | 8 | 213 | 215 | 178 |
| | 9 | 219 | 295 | 231 |
| | 10 | 222 | 231 | 187 |
| | 11 | 218 | 297 | 245 |
| | 12 | 229 | 233 | 191 |
| Mean ± SEM | | 221.80 ± 2.70 | 242.50 ± 18.37 | 198.00 ± 13.70# |
| Test drug | 13 | 283 | 291 | 253 |
| (100 mg/Kg) | 14 | 233 | 243 | 212 |
| | 15 | 206 | 188 | 165 |
| | 16 | 209 | 203 | 225 |
| | 17 | 232 | 235 | 198 |
| | 18 | 250 | 258 | 182 |
| Mean ± SEM | | 235.50 ± 11.60 | 236.33 ± 15.22 | 205.83 ± 12.81 |
| Test drug | 19 | 252 | 252 | 252 |
| (200 mg/Kg) | 20 | 226 | 235 | 205 |
| | 21 | 223 | 242 | 199 |
| | 22 | 232 | 242 | 204 |
| | 23 | 237 | 267 | 209 |
| | 24 | 216 | 219 | 189 |
| Mean ± SEM | | 231.00 ± 5.14 | 242.83 ± 6.58 | 209.67 ± 8.92 |

The results are expressed in Individual as well as Mean ± SEM (n = 6);
Statistical analysis was done using graph pad prism 5.0 version and Tukey post hoc test was performed.
p < 0.05, ##p < 0.01 compared with Normal control: p < 0.05 (*) & 0.01 (**) compared with Gentamicin (100 mg/kg) i.p

TABLE 5

Effect of Test drug Treatment on Urine Output In Nephrotoxicity Induced Rats.

| Treatment | Animal No | Urine Out Put (ml) | | Urobilinogen (umol/L) | |
|---|---|---|---|---|---|
| | | 7 | 14 | 7 | 14 |
| 0.5% CMC | 1 | 4.00 | 6.00 | 34 | 3.4 |
| | 2 | 4.00 | 6.00 | 34 | 3.4 |
| | 3 | 8.80 | 6.40 | 34 | 3.4 |
| | 4 | 7.20 | 5.60 | 34 | 3.4 |
| | 5 | 12.00 | 8.00 | 34 | 3.4 |
| | 6 | 12.00 | 8.00 | 34 | 3.4 |
| Mean ± SEM | | 8.00 ± 1.48 | 6.67 ± 0.43 | 34.00 | 3.40 |
| Gentamicin (100 mg/kg) i.p | 7 | 11.20 | 4.00 | 34 | 34 |
| | 8 | 8.80 | 4.00 | 34 | 34 |
| | 9 | 26.00 | 9.20 | 34 | 34 |
| | 10 | 22.00 | 8.80 | 34 | 34 |
| | 11 | 12.80 | 10.00 | 34 | 34 |
| | 12 | 14.00 | 10.00 | 34 | 34 |
| Mean ± SEM | | 15.80 ± 2.74## | 7.67 ± 1.17 | 34.00 | 34.00 |
| Test drug (100 mg/Kg) | 13 | 28.00 | 22.40 | 34 | 34 |
| | 14 | 28.00 | 21.60 | 34 | 34 |
| | 15 | 20.40 | 14.00 | 34 | 34 |
| | 16 | 19.60 | 14.00 | 34 | 34 |
| | 17 | 25.20 | 10.00 | 34 | 34 |
| | 18 | 26.00 | 12.00 | 34 | 34 |
| Mean ± SEM | | 24.53 ± 1.51** | 15.67 ± 2.09** | 34.00 | 34.00 |
| Test drug (200 mg/Kg) | 19 | 12.80 | 14.80 | 34 | 34 |
| | 20 | 29.60 | 15.20 | 34 | 34 |
| | 21 | 14.00 | 7.20 | 34 | 34 |
| | 22 | 14.00 | 6.80 | 34 | 34 |

TABLE 5-continued

Effect of Test drug Treatment on Urine Output In Nephrotoxicity Induced Rats.

| Treatment | Animal No | Urine Out Put (ml) 7 | Urine Out Put (ml) 14 | Urobilinogen (umol/L) 7 | Urobilinogen (umol/L) 14 |
|---|---|---|---|---|---|
| | 23 | 16.40 | 4.00 | 34 | 34 |
| | 24 | 16.80 | 4.00 | 34 | 34 |
| Mean ± SEM | | 17.27 ± 2.55 | 8.67 ± 2.08 | 34.00 | 34.00 |

The results are expressed in Individual values as well as Mean±SEM (n=6); Statistical analysis was done using graph pad prism 5.0 version and Tukey post hoc test was performed

TABLE 6

Effect of Test drug Treatment on Urinary Parameters In Nephrotoxicity Induced Rats

| Treatment | Animal No | BIL (umol/L) 7 | BIL (umol/L) 14 | BLD (Ery/μL) 7 | BLD (Ery/μL) 14 | NIT 7 | NIT 14 | GLUCOSE (mmol/L) 7 | GLUCOSE (mmol/L) 14 | MALB (g/L) 7 | MALB (g/L) 14 |
|---|---|---|---|---|---|---|---|---|---|---|---|
| 0.5% CMC | 1 | Negative | Negative | Negative | Negative | Negative | Negative | Negative | Negative | >0.15 | Negative |
| | 2 | Negative | Negative | Negative | Negative | Negative | Negative | Negative | Negative | >0.15 | Negative |
| | 3 | Negative | Negative | Negative | Negative | Negative | Negative | Negative | Negative | >0.15 | Negative |
| | 4 | Negative | Negative | Negative | Negative | Negative | Negative | Negative | Negative | >0.15 | Negative |
| | 5 | Negative | Negative | Negative | Negative | Negative | Negative | Negative | Negative | >0.15 | Negative |
| | 6 | Negative | Negative | Negative | Negative | Negative | Negative | Negative | Negative | >0.15 | Negative |
| Gentamicin (100 mg/kg) i.p | 7 | Negative | Negative | Negative | Negative | Negative | Negative | Negative | 5.6 | >0.15 | >0.15 |
| | 8 | Negative | Negative | Negative | Negative | Negative | Negative | Negative | 5.6 | >0.15 | >0.15 |
| | 9 | Negative | Negative | Negative | Negative | Negative | Negative | Negative | 5.6 | >0.15 | >0.15 |
| | 10 | Negative | Negative | Negative | Negative | Negative | Negative | Negative | 5.6 | >0.15 | >0.15 |
| | 11 | Negative | Negative | Negative | Negative | Negative | Negative | Negative | 5.6 | >0.15 | >0.15 |
| | 12 | Negative | Negative | Negative | Negative | Negative | Negative | Negative | 5.6 | >0.15 | >0.15 |
| Test drug (100 mg/Kg) | 13 | Negative | Negative | Negative | Negative | Negative | Negative | 5.6 | 5.6 | >0.15 | >0.15 |
| | 14 | Negative | Negative | Negative | Negative | Negative | Negative | 5.6 | 5.6 | >0.15 | >0.15 |
| | 15 | Negative | Negative | Negative | Negative | Negative | Negative | Negative | 5.6 | >0.15 | >0.15 |
| | 16 | Negative | Negative | Negative | Negative | Negative | Negative | Negative | 5.6 | >0.15 | >0.15 |
| | 17 | Negative | Negative | Negative | Negative | Negative | Negative | Negative | 5.6 | >0.15 | >0.15 |
| | 18 | Negative | Negative | Negative | Negative | Negative | Negative | Negative | 5.6 | >0.15 | >0.15 |
| Test drug (200 mg/Kg) | 19 | Negative | Negative | Negative | Negative | Negative | Negative | 5.6 | 5.6 | >0.15 | >0.15 |
| | 20 | Negative | Negative | Negative | Negative | Negative | Negative | 5.6 | 5.6 | >0.15 | >0.15 |
| | 21 | Negative | Negative | Negative | Negative | Negative | Negative | Negative | 5.6 | >0.15 | >0.15 |
| | 22 | Negative | Negative | Negative | Negative | Negative | Negative | Negative | 5.6 | >0.15 | >0.15 |
| | 23 | Negative | Negative | Negative | Negative | Negative | Negative | Negative | 5.6 | >0.15 | >0.15 |
| | 24 | Negative | Negative | Negative | Negative | Negative | Negative | Negative | 5.6 | >0.15 | >0.15 |

| Treatment | Animal No | SG 7 | SG 14 | pH 7 | pH 14 | KET (umol/L) 7 | KET (umol/L) 14 | PRO (g/L) 7 | PRO (g/L) 14 | LEU (Lue/μL) 7 | LEU (Lue/μL) 14 |
|---|---|---|---|---|---|---|---|---|---|---|---|
| 0.5% CMC | 1 | 1.025 | 1.030 | 5.1 | 6 | Negative | Negative | 0.3 | Negative | Ca15 | Negative |
| | 2 | 1.025 | 1.030 | 5.1 | 6 | Negative | Negative | 0.3 | Negative | Ca15 | Negative |
| | 3 | 1.025 | 1.030 | 7.5 | 6 | 0.5 | Negative | 3 | Negative | Ca15 | Negative |
| | 4 | 1.025 | 1.030 | 7.5 | 6 | 0.5 | Negative | 3 | Negative | Ca15 | Negative |
| | 5 | 1.015 | 1.030 | 6 | 6 | 0.5 | Negative | 0.3 | Negative | Ca15 | Negative |
| | 6 | 1.015 | 1.030 | 6 | 6 | 0.5 | Negative | 0.3 | Negative | Ca15 | Negative |
| Mean ± SEM | | 1.02 ± 0.00 | 1.03 ± 0.00 | 6.20 ± 0.44 | 6.00 ± 0.00 | 0.50 ± 0.00 | Negative | 1.20 ± 0.57 | 0.00 ± 0.00 | Ca15 | Negative |
| Gentamicin (100 mg/kg) i.p | 7 | 1.025 | 1.030 | 5.5 | 5.5 | 0.5 | Negative | 1 | 1 | Ca15 | Ca15 |
| | 8 | 1.025 | 1.030 | 5.5 | 5.5 | 0.5 | Negative | 1 | 1 | Ca15 | Ca15 |
| | 9 | 1.015 | 1.030 | 6 | 5.5 | 0.5 | Negative | 0.3 | 1 | Ca15 | Ca15 |
| | 10 | 1.015 | 1.030 | 6 | 5.5 | 0.5 | Negative | 0.3 | 1 | Ca15 | Ca15 |
| | 11 | 1.02 | 1.030 | 6.5 | 5.5 | 0.5 | Negative | 1 | 1 | Ca15 | Ca15 |
| | 12 | 1.02 | 1.030 | 6.5 | 5.5 | 0.5 | Negative | 1 | 1 | Ca15 | Ca15 |
| Mean ± SEM | | 1.02 ± 0.00 | 1.03 ± 0.00 | 6.00 ± 0.18 | 5.50 ± 0.00 | 0.50 ± 0.00 | Negative | 0.77 ± 0.15 | 1.00 ± 0.00# | Ca15 | Ca15 |
| Test drug (100 mg/Kg) | 13 | 1.025 | 1.015 | 6 | 6 | 0.5 | 0.5 | 3 | 1 | Ca 70 | Ca70 |
| | 14 | 1.025 | 1.015 | 6 | 6 | 0.5 | 0.5 | 3 | 1 | Ca 70 | Ca70 |
| | 15 | 1.015 | 1.015 | 6 | 6 | 0.5 | 0.5 | 0.3 | 1 | Ca15 | Ca70 |
| | 16 | 1.015 | 1.015 | 6 | 6 | 0.5 | 0.5 | 0.3 | 1 | Ca15 | Ca70 |
| | 17 | 1.015 | 1.015 | 5 | 6 | 0.5 | 0.5 | 0.3 | 1 | Ca15 | Ca70 |
| | 18 | 1.015 | 1.015 | 5 | 6 | 0.5 | 0.5 | 0.3 | 1 | Ca15 | Ca70 |

TABLE 6-continued

Effect of Test drug Treatment on Urinary Parameters In Nephrotoxicity Induced Rats

|  |  |  |  |  |  |  |  |  |  |  |  |
|---|---|---|---|---|---|---|---|---|---|---|---|
| Mean ± SEM |  | 1.02 ± 0.00 | 1.02 ± 0.00 | 5.67 ± 0.21 | 6.00 ± 0.00 | 0.50 ± 0.00 | 0.50 ± 0.00 | 1.20 ± 0.57 | 1.00 ± 0.00 | Ca30 ± 11.60 | Ca70 |
| Test drug (200 mg/Kg) | 19 | 1.03 | 1.025 | 6.5 | 5.5 | 0.5 | Negative | 1 | 3 | Ca15 | Ca70 |
|  | 20 | 1.03 | 1.025 | 6.5 | 5.5 | 0.5 | Negative | 1 | 3 | Ca15 | Ca70 |
|  | 21 | 1.03 | 1.025 | 6 | 5.5 | 0.5 | Negative | 1 | 3 | Ca15 | Ca70 |
|  | 22 | 1.03 | 1.025 | 6 | 5.5 | 0.5 | Negative | 1 | 3 | Ca15 | Ca70 |
|  | 23 | 1.015 | 1.025 | 6.5 | 5.5 | 0.5 | Negative | 1 | 3 | Ca15 | Ca70 |
|  | 24 | 1.015 | 1.025 | 6.5 | 5.5 | 0.5 | Negative | 1 | 3 | Ca15 | Ca70 |
| Mean ± SEM |  | 1.03 ± 0.00 | 1.03 ± 0.00 | 6.33 ± 0.11 | 5.50 ± 0.00 | 0.50 ± 0.00 | Negative | 1.00 ± 0.00 | 3.00 ± 0.00** | Ca15 | Ca70 |

The results are expressed in Individual values as well as Mean±SEM (n=6); Statistical analysis was done using graph pad prism 5.0 version and Tukey post hoc test was performed. #$p<0.05$, ##$p<0.01$ compared with Normal control: $p<0.05$ (*) & 0.01 (**) compared with Gentamicin (100 mg/kg) i.p

TABLE 7

Effect of Test drug Treatment on Urine Biochemistry in Nephrotoxicity

| Treatment | Animal No | Urea (mg/ml) 7 | 14 | Creatinine (mg/ml) 7 | 14 | ACP (U/L) 7 | 14 | Albumin (mg/dl) 7 | 14 |
|---|---|---|---|---|---|---|---|---|---|
| 0.5% CMC | 1 | 21.61 | 20.57 | 0.35 | 0.98 | 50.00 | 60.00 | 1.23 | 1.31 |
|  | 2 | 15.57 | 22.66 | 0.4 | 1.195 | 49.00 | 49.00 | 1.13 | 1.15 |
|  | 3 | 14.25 | 42.62 | 1.55 | 0.7 | 58.00 | 58.00 | 1.12 | 1.14 |
|  | 4 | 28.65 | 24.56 | 0.66 | 0.89 | 51.00 | 41.00 | 1.64 | 1.74 |
|  | 5 | 25.80 | 29.9 | 1.5 | 1.24 | 38.00 | 48.00 | 1.11 | 1.41 |
|  | 6 | 72.50 | 30.65 | 0.605 | 0.78 | 43.00 | 53.00 | 1.28 | 1.48 |
| Mean ± SEM |  | 29.73 ± 8.85 | 28.49 ± 3.26 | 0.84 ± 0.22 | 0.96 ± 0.09 | 48.17 ± 2.82 | 51.50 ± 2.86 | 1.25 ± 0.08 | 1.37 ± 0.09 |
| Gentamicin (100 mg/kg) i.p | 7 | 46.375 | 66.7 | 1.62 | 1.13 | 61.00 | 56.00 | 1.91 | 2.91 |
|  | 8 | 44.565 | 60.965 | 1.17 | 1.56 | 53.00 | 75.00 | 0.83 | 2.93 |
|  | 9 | 32.35 | 49.345 | 1.055 | 1.945 | 55.00 | 73.00 | 1.54 | 1.44 |
|  | 10 | 67.605 | 51.21 | 1.39 | 2.28 | 51.00 | 45.00 | 1.18 | 1.18 |
|  | 11 | 48.48 | 59.8 | 0.945 | 1.67 | 54.00 | 66.33 | 1.89 | 1.99 |
|  | 12 | 49.5 | 52.26 | 1.59 | 1.28 | 61.00 | 72.33 | 2.02 | 2.02 |
| Mean ± SEM |  | 48.15 ± 4.64## | 56.71 ± 2.78## | 1.30 ± 0.12 | 1.64 ± 0.17# | 54.17 ± 1.51 | 64.61 ± 4.83 | 1.56 ± 0.19 | 2.08 ± 0.30## |
| Test drug (100 mg/Kg) | 13 | 36.255 | 40.685 | 0.785 | 0.67 | 46.00 | 51.00 | 0.88 | 0.89 |
|  | 14 | 39.77 | 32.68 | 0.615 | 1.03 | 65.00 | 43.00 | 1.66 | 0.92 |
|  | 15 | 33.13 | 27.105 | 0.855 | 0.635 | 35.00 | 46.00 | 0.67 | 0.55 |
|  | 16 | 30.825 | 26.45 | 0.715 | 0.995 | 51.00 | 50.00 | 1.66 | 1.03 |
|  | 17 | 65.8 | 33.86 | 1.535 | 1.23 | 56.33 | 64.00 | 0.77 | 1.11 |
|  | 18 | 55.105 | 30.06 | 1.38 | 0.815 | 62.33 | 71.00 | 1.66 | 1.99 |
| Mean ± SEM |  | 43.48 ± 5.68 | 31.81 ± 2.14* | 0.98 ± 0.16 | 0.90 ± 0.09* | 52.61 ± 4.54 | 54.17 ± 4.47 | 1.22 ± 0.20 | 1.08 ± 0.20** |
| Test drug (100 mg/Kg) | 19 | 26.35 | 31.825 | 1.37 | 0.505 | 44.33 | 54.33 | 0.90 | 0.91 |
|  | 20 | 24.01 | 37.57 | 1.22 | 0.645 | 56.33 | 56.33 | 1.68 | 0.94 |
|  | 21 | 26.225 | 27.425 | 1.7 | 0.6 | 45.00 | 63.00 | 0.73 | 0.66 |
|  | 22 | 35.105 | 33.615 | 1.6 | 0.88 | 41.00 | 45.00 | 1.68 | 1.05 |
|  | 23 | 49.005 | 32.15 | 1.66 | 0.875 | 56.33 | 66.33 | 0.79 | 1.13 |
|  | 24 | 46.555 | 56.215 | 1.445 | 1.055 | 52.00 | 62.00 | 1.68 | 2.01 |
| Mean ± SEM |  | 34.54 ± 4.48 | 36.47 ± 4.17* | 1.50 ± 0.08 | 0.76 ± 0.09* | 49.17 ± 2.70 | 57.83 ± 3.14 | 1.24 ± 0.20 | 1.12 ± 0.19** |

| Treatment | Animal No | ALP (U/L) 7 | 14 | g-GT (U/L) 7 | 14 | Uric acid (mg/dl) 7 | 14 |
|---|---|---|---|---|---|---|---|
| 0.5% CMC | 1 | 1.00 | 1.00 | 37.00 | 27.00 | 6.69 | 6.09 |
|  | 2 | 0.00 | 0.00 | 36.00 | 56.00 | 9.25 | 9.15 |
|  | 3 | 0.00 | 0.00 | 34.00 | 64.00 | 8.78 | 8.38 |
|  | 4 | 1.00 | 1.00 | 40.00 | 50.00 | 6.00 | 6.00 |
|  | 5 | 1.00 | 1.00 | 37.00 | 37.00 | 6.00 | 10.44 |
|  | 6 | 1.00 | 1.00 | 39.00 | 39.00 | 9.00 | 9.00 |
| Mean ± SEM |  | 0.67 ± 0.21 | 0.67 ± 0.21 | 37.17 ± 0.87 | 45.57 ± 5.17 | 7.62 ± 0.63 | 8.18 ± 0.73 |
| Gentamicin (100 mg/kg) i.p | 7 | 1.00 | 1.00 | 13.00 | 13.00 | 12 | 13.37 |
|  | 8 | 1.00 | 1.00 | 26.00 | 26.00 | 13 | 14.86 |
|  | 9 | 1.00 | 2.00 | 23.00 | 23.00 | 12.12 | 13.11 |
|  | 10 | 1.00 | 3.00 | 26.00 | 36.00 | 12.13 | 12.30 |
|  | 11 | 1.00 | 1.00 | 34.00 | 34.00 | 11.13 | 11.32 |
|  | 12 | 1.00 | 1.00 | 19.00 | 29.00 | 11.99 | 10.99 |

TABLE 7-continued

Effect of Test drug Treatment on Urine Biochemistry in Nephrotoxicity

| | | | | | | |
|---|---|---|---|---|---|---|
| Mean ± SEM | | 1.00 ± 0.00 | 1.50 ± 0.34[#] | 23.50 ± 2.91[##] | 26.83 ± 3.40[##] | 12.06 ± 0.24[##] | 12.66 ± 0.58[#] |
| Test drug (100 mg/Kg) | 13 | 1.00 | 0.00 | 32.00 | 32.00 | 4.75 | 5.75 |
| | 14 | 1.00 | 1.00 | 23.00 | 23.00 | 4.43 | 4.73 |
| | 15 | 0.00 | 2.00 | 32 | 32 | 7.25 | 7.85 |
| | 16 | 1.00 | 1.00 | 22.00 | 26.00 | 6.22 | 6.92 |
| | 17 | 0.00 | 1.00 | 33.00 | 36.00 | 6.88 | 6.98 |
| | 18 | 0.00 | 1.00 | 32.00 | 31.00 | 7.98 | 7.88 |
| Mean ± SEM | | 0.50 ± 0.22 | 1.00 ± 0.26 | 29.00 ± 2.07 | 30.00 ± 1.91 | 6.25 ± 0.58* | 6.69 ± 0.50* |
| Test drug (200 mg/Kg) | 19 | 0.00 | 1.00 | 36.00 | 42.00 | 6 | 6.4 |
| | 20 | 1.00 | 1.00 | 25.00 | 34.00 | 7.69 | 7.09 |
| | 21 | 0.00 | 1.00 | 27.00 | 32.00 | 6.09 | 6.9 |
| | 22 | 1.00 | 1.00 | 29.00 | 27.00 | 6.88 | 6.08 |
| | 23 | 1.00 | 0.00 | 33.00 | 24.00 | 6.67 | 6.77 |
| | 24 | 1.00 | 0.00 | 38.00 | 37.00 | 5.44 | 5.04 |
| Mean ± SEM | | 0.67 ± 0.21 | 0.67 ± 0.21* | 31.33 ± 2.11* | 32.67 ± 2.68 | 6.46 ± 0.32 | 6.38 ± 0.31 |

The results are expressed in Individual as well as Mean±SEM (n=6); Statistical analysis was done using graph pad prism 5.0 version and Tukey post hoc test was performed. #p<0.05, ##p<0.01 compared with normal control: p<0.05 (*) & 0.01 (**) compared with Gentamicin (100 mg/kg) i.p

TABLE 8

Effect of Test drug Treatment on Organ Weight in Nephrotoxicity Induced Rats

| Treatment | Animal No | Kidney weight (g) |
|---|---|---|
| Normal control | 1 | 2.00 |
| | 2 | 2.30 |
| | 3 | 2.30 |
| | 4 | 2.30 |
| | 5 | 1.40 |
| | 6 | 2.20 |
| Mean ± SEM | | 2.08 ± 0.14 |
| Gentamicin (100 mg/kg i.p) | 7 | 1.90 |
| | 8 | 2.50 |
| | 9 | 2.70 |
| | 10 | 2.30 |

TABLE 8-continued

Effect of Test drug Treatment on Organ Weight in Nephrotoxicity Induced Rats

| Treatment | Animal No | Kidney weight (g) |
|---|---|---|
| | 11 | 2.70 |
| | 12 | 2.90 |
| Mean ± SEM | | 2.50 ± 0.15 |
| Test drug (100 mg/kg) | 13 | 3.30 |
| | 14 | 2.50 |
| | 15 | 2.40 |
| | 16 | 3.00 |
| | 17 | 3.10 |
| | 18 | 2.40 |
| Mean ± SEM | | 2.78 ± 0.16 |
| Test drug (200 mg/kg) | 19 | 2.10 |
| | 20 | 2.80 |
| | 21 | 2.60 |
| | 22 | 2.70 |
| | 23 | 2.80 |
| | 24 | 2.40 |
| Mean ± SEM | | 2.57 ± 0.11 |

TABLE 9

Effect of Test drug Treatment on Blood Biochemistry In Nephrotoxicity Induced Rats

| Treatment | Animal No | ACP U/L | Albumin (g/dL) | ALP (U/L) | Total protein (g/dl) | γ-GT (U/L) |
|---|---|---|---|---|---|---|
| 0.5% CMC | 1 | 38.00 | 2.57 | 59.00 | 5.67 | 1.00 |
| | 2 | 33.00 | 2.49 | 55.00 | 5.40 | 1.00 |
| | 3 | 38.00 | 2.51 | 55.00 | 5.53 | 1.00 |
| | 4 | 32.00 | 2.45 | 57.00 | 5.34 | 1.00 |
| | 5 | 50.00 | 2.71 | 69.00 | 6.32 | 1.00 |
| | 6 | 31.00 | 2.46 | 65.00 | 5.30 | 1.00 |
| Mean ± SEM | | 37.00 ± 2.88 | 2.53 ± 0.04 | 60.00 ± 2.35 | 5.59 ± 0.16 | 1.00 ± 0.00 |
| Gentamicin (100 mg/kg) i.p | 7 | 42.00 | 2.58 | 83.00 | 6.25 | 2.00 |
| | 8 | 30.00 | 2.44 | 92.00 | 5.27 | 4.00 |
| | 9 | 40.00 | 2.41 | 92.00 | 5.66 | 1.00 |
| | 10 | 37.00 | 2.50 | 83.00 | 5.87 | 3.00 |
| | 11 | 40.00 | 2.63 | 69.00 | 5.94 | 2.00 |
| | 12 | 46.00 | 2.53 | 67.00 | 5.45 | 3.00 |
| Mean ± SEM | | 39.17 ± 2.20 | 2.52 ± 0.03 | 81.00 ± 4.43[##] | 5.74 ± 0.15 | 2.50 ± 0.43[##] |
| Test drug (100 mg/Kg) | 13 | 45.00 | 2.38 | 67.00 | 5.52 | 1.00 |
| | 14 | 34.00 | 2.28 | 84.00 | 6.06 | 1.00 |
| | 15 | 43.00 | 2.61 | 94.00 | 5.72 | 1.00 |
| | 16 | 33.00 | 2.55 | 62.00 | 5.37 | 2.00 |

TABLE 9-continued

Effect of Test drug Treatment on Blood Biochemistry
In Nephrotoxicity Induced Rats

| Treatment | Animal No | ACP U/L | Albumin (g/dL) | ALP (U/L) | Total protein (g/dl) | γ-GT (U/L) |
|---|---|---|---|---|---|---|
| | 17 | 30.00 | 2.51 | 69.00 | 5.50 | 1.00 |
| | 18 | 45.00 | 2.59 | 89.00 | 5.56 | 1.00 |
| Mean ± SEM | | 38.33 ± 2.75 | 2.49 ± 0.05 | 77.50 ± 5.38 | 5.62 ± 0.10 | 1.17 ± 0.17** |
| Test drug (200 mg/Kg) | 19 | 41.00 | 2.66 | 70.00 | 5.72 | 1.00 |
| | 20 | 36.00 | 2.71 | 76.00 | 6.41 | 1.00 |
| | 21 | 52.00 | 2.98 | 87.00 | 6.91 | 1.00 |
| | 22 | 42.00 | 2.97 | 91.00 | 6.39 | 1.00 |
| | 23 | 45.00 | 2.47 | 96.00 | 5.80 | 1.00 |
| | 24 | 35.00 | 2.73 | 97.00 | 5.62 | 1.00 |
| Mean ± SEM | | 41.83 ± 2.55 | 2.75 ± .080 | 86.17 ± 4.48 | 6.14 ± 0.21 | 1.00 ± 0.00** |

The results are expressed in Individual as well as Mean±SEM (n=6); Statistical analysis was done using graph pad prism 5.0 version and Tukey post hoc test was performed. # p<0.05, ##p<0.01 compared with Normal control: p<0.05 (*) & 0.01 (**) compared with Gentamicin (100 mg/kg) i.p

| Treatment | Animal No | Creatinine (mg/dl) | Urea (mg/dl) | Uric acid (mg/dl) | Globulin (g/dl) |
|---|---|---|---|---|---|
| 0.5% CMC | 1 | 0.64 | 33.00 | 1.15 | 3.10 |
| | 2 | 0.64 | 42.00 | 1.85 | 2.91 |
| | 3 | 0.63 | 29.00 | 1.42 | 3.02 |
| | 4 | 0.88 | 31.00 | 1.21 | 2.88 |
| | 5 | 0.74 | 34.00 | 1.83 | 3.61 |
| | 6 | 0.69 | 35.00 | 1.75 | 2.84 |
| Mean ± SEM | | 0.70 ± 0.04 | 34.00 ± 1.83 | 1.54 ± 0.13 | 3.06 ± 0.12 |
| Gentamicin (100 mg/kg) i.p | 7 | 0.99 | 44.00 | 1.43 | 3.67 |
| | 8 | 0.84 | 39.00 | 1.84 | 2.83 |
| | 9 | 1.00 | 67.00 | 2.48 | 3.25 |
| | 10 | 0.93 | 60.00 | 2.02 | 3.37 |
| | 11 | 0.87 | 46.00 | 1.46 | 3.31 |
| | 12 | 0.80 | 45.00 | 2.35 | 2.91 |
| Mean ± SEM | | 0.91 ± 0.03## | 50.17 ± 4.42## | 1.93 ± 0.18## | 3.22 ± 0.13 |
| Test drug (100 mg/Kg) | 13 | 0.90 | 41.00 | 2.30 | 3.13 |
| | 14 | 1.02 | 52.00 | 2.57 | 3.79 |
| | 15 | 0.81 | 43.00 | 1.03 | 3.11 |
| | 16 | 0.71 | 27.00 | 1.45 | 2.82 |
| | 17 | 0.88 | 40.00 | 1.29 | 3.00 |
| | 18 | 0.76 | 37.00 | 1.60 | 2.96 |
| Mean ± SEM | | 0.85 ± 0.05 | 40.00 ± 3.33 | 1.71 ± 0.25 | 3.13 ± 0.14 |
| Test drug (200 mg/Kg) | 19 | 0.77 | 44.00 | 1.63 | 3.06 |
| | 20 | 0.65 | 35.00 | 0.84 | 3.70 |
| | 21 | 1.10 | 43.00 | 1.18 | 3.93 |
| | 22 | 0.88 | 43.00 | 1.08 | 3.42 |
| | 23 | 0.87 | 42.00 | 1.24 | 3.33 |
| | 24 | 0.71 | 39.00 | 1.74 | 2.89 |
| Mean ± SEM | | 0.83 ± 0.07 | 41.00 ± 1.39 | 1.29 ± 0.14** | 3.39 ± 0.16 |

The results are expressed in Individual as well as Mean±SEM (n=6); Statistical analysis was done using graph pad prism 5.0 version and Tukey post hoc test was performed. # p<0.05, ##p<0.01 compared with Normal control: p<0.05 (*) & 0.01 (**) compared with Gentamicin (100 mg/kg) i.p

TABLE 10

Effect of Test drug Treatment on Serum Electrolytes
in Nephrotoxicity Induced Rats

| Treatment | Animal No | K mmol/L | Na mmol/L | Cl mmol/L | nCa mmol/L | tCa mmol/L | pH |
|---|---|---|---|---|---|---|---|
| 0.5% CMC | 1 | 12.27 | 144.61 | 101.56 | 3.3 | 6.65 | 7.91 |
| | 2 | 12.67 | 146.68 | 102.34 | 1.7 | 3.4 | 7.94 |
| | 3 | 14.01 | 147.27 | 105.49 | 2.25 | 4.55 | 7.95 |

TABLE 10-continued

Effect of Test drug Treatment on Serum Electrolytes in Nephrotoxicity Induced Rats

| Treatment | Animal No | K mmol/L | Na mmol/L | Cl mmol/L | nCa mmol/L | tCa mmol/L | pH |
|---|---|---|---|---|---|---|---|
| | 4 | 11.83 | 147.27 | 107.10 | 2.5 | 5 | 7.92 |
| | 5 | 11.89 | 145.79 | 103.11 | 2.7 | 4.85 | 7.89 |
| | 6 | 12.99 | 147.87 | 106.70 | 0.65 | 1.35 | 7.91 |
| Mean ± SEM | | 12.61 ± 0.33 | 146.58 ± 0.49 | 104.38 ± 0.96 | 2.18 ± 0.37 | 4.30 ± 0.73 | 7.92 ± 0.01 |
| Gentamicin (100 mg/kg) i.p | 7 | 12.39 | 146.38 | 102.34 | 5.75 | 11.50 | 7.92 |
| | 8 | 11.02 | 147.87 | 103.11 | 4 | 7.95 | 7.91 |
| | 9 | 11.04 | 147.27 | 97.80 | 5.9 | 11.85 | 7.94 |
| | 10 | 12.16 | 146.98 | 103.11 | 2.55 | 5.10 | 7.88 |
| | 11 | 13.12 | 145.79 | 99.66 | 4.3 | 8.65 | 7.92 |
| | 12 | 12.04 | 148.47 | 100.42 | 3.5 | 7.00 | 7.98 |
| Mean ± SEM | | 11.96 ± 0.33 | 147.13 ± 0.40 | 101.07 ± 0.88 | 4.33 ± 0.53## | 8.68 ± 1.07## | 7.93 ± 0.01 |
| Test drug (100 mg/Kg) | 13 | 12.72 | 149.78 | 106.77 | 2.8 | 5.65 | 7.89 |
| | 14 | 11.36 | 146.63 | 101.04 | 3.05 | 6.05 | 7.90 |
| | 15 | 12.37 | 158.40 | 113.82 | 3.5 | 7.00 | 7.89 |
| | 16 | 12.45 | 145.34 | 105.21 | 2.7 | 6.75 | 7.92 |
| | 17 | 17.38 | 147.20 | 112.37 | 4.05 | 8.10 | 7.79 |
| | 18 | 13.86 | 153.58 | 99.77 | 2.25 | 4.50 | 7.93 |
| Mean ± SEM | | 13.36 ± 0.87 | 150.16 ± 2.03 | 106.50 ± 2.34 | 3.06 ± 0.26 | 6.34 ± 0.50 | 7.89 ± 0.02 |
| Test drug (200 mg/Kg) | 19 | 10.16 | 154.18 | 99.77 | 1.65 | 3.30 | 7.91 |
| | 20 | 17.69 | 145.79 | 93.27 | 3.1 | 6.20 | 7.99 |
| | 21 | 14.18 | 146.91 | 98.93 | 0.3 | 0.60 | 8.11 |
| | 22 | 13.48 | 141.36 | 92.50 | 1.5 | 2.95 | 8.08 |
| | 23 | 11.56 | 140.27 | 90.96 | 1.9 | 3.85 | 8.00 |
| | 24 | 13.48 | 145.68 | 95.14 | 4.4 | 8.80 | 8.04 |
| Mean ± SEM | | 13.43 ± 1.05 | 145.70 ± 2.01 | 95.10 ± 1.46 | 2.14 ± 0.58** | 4.28 ± 1.16** | 8.02 ± 0.03 |

The results are expressed in Individual as well as Mean±SEM (n=6); Statistical analysis was done using graph pad prism 5.0 version and Tukey post hoc test was performed. # p<0.05, ##p<0.01 compared with Normal control: p<0.05 (*) & 0.01 (**) compared with Gentamicin (100 mg/kg) i.p

TABLE 11

Effect of Test drug Treatment on Renal Stress Marker In Nephrotoxicity Induced Rats

| Treatment | Animal No | GSH (mg/g) | GPx (mg/mt/mg ptn) | TBARS (mg/g) | SOD U/mt/g ptn | Catalase mm/mt/mg ptn |
|---|---|---|---|---|---|---|
| 0.5% CMC | 1 | 1.06 | 13.72 | 0.73 | 19.02 | 146.54 |
| | 2 | 1.53 | 14.80 | 0.69 | 10.84 | 326.90 |
| | 3 | 1.65 | 13.26 | 0.61 | 17.75 | 189.92 |
| | 4 | 1.97 | 11.13 | 0.43 | 32.56 | 433.56 |
| | 5 | 2.99 | 20.49 | 0.48 | 36.73 | 417.93 |
| | 6 | 2.64 | 19.27 | 0.52 | 31.92 | 414.95 |
| Mean ± SEM | | 1.97 ± 0.29 | 15.44 ± 1.49 | 0.58 ± 0.05 | 24.80 ± 4.21 | 338.63 ± 41.58 |
| Gentamicin (100 mg/kg) i.p | 7 | 0.83 | 5.79 | 0.79 | 9.02 | 179.44 |
| | 8 | 1.90 | 7.12 | 0.90 | 10.34 | 225.04 |
| | 9 | 0.16 | 6.82 | 0.93 | 14.22 | 280.37 |
| | 10 | 1.78 | 11.42 | 0.73 | 12.90 | 287.86 |
| | 11 | 0.94 | 7.24 | 0.87 | 22.26 | 339.18 |
| | 12 | 0.17 | 3.06 | 0.88 | 15.12 | 127.34 |
| Mean ± SEM | | 0.96 ± 0.31## | 6.91 ± 1.10## | 0.85 ± 0.03# | 13.97 ± 1.91## | 239.87 ± 31.80 |
| Test drug (100 mg/Kg) | 13 | 1.38 | 10.69 | 0.60 | 18.10 | 254.22 |
| | 14 | 2.36 | 8.72 | 0.82 | 14.96 | 206.63 |
| | 15 | 2.28 | 10.53 | 0.53 | 18.08 | 272.51 |
| | 16 | 1.16 | 5.83 | 0.55 | 10.02 | 254.38 |
| | 17 | 1.58 | 4.60 | 0.52 | 17.91 | 205.98 |
| | 18 | 0.91 | 5.74 | 0.74 | 8.68 | 257.08 |
| Mean ± SEM | | 1.61 ± 0.24** | 7.68 ± 1.08 | 0.63 ± 0.05* | 14.63 ± 1.75 | 241.80 ± 11.56 |
| Test drug (200 mg/Kg) | 19 | 2.85 | 8.79 | 1.07 | 13.73 | 379.07 |
| | 20 | 2.35 | 7.58 | 0.95 | 15.16 | 242.37 |
| | 21 | 2.06 | 7.66 | 0.47 | 19.03 | 245.98 |
| | 22 | 1.72 | 10.06 | 0.51 | 19.34 | 259.08 |

TABLE 11-continued

Effect of Test drug Treatment on Renal Stress Marker In Nephrotoxicity Induced Rats

| Treatment | Animal No | GSH (mg/g) | GPx (mg/mt/mg ptn) | TBARS (mg/g) | SOD U/mt/g ptn | Catalase mm/mt/mg ptn |
|---|---|---|---|---|---|---|
| | 23 | 2.02 | 6.07 | 0.59 | 11.98 | 177.58 |
| | 24 | 1.91 | 8.06 | 1.05 | 15.06 | 271.82 |
| Mean ± SEM | | 2.15 ± 0.16** | 8.04 ± 0.54 | 0.77 ± 0.11 | 15.72 ± 1.19 | 262.65 ± 26.82 |

The results are expressed in Individual as well as Mean±SEM (n=6); Statistical analysis was done using graph pad prism 5.0 version and Tukey post hoc test was performed. # $p<0.05$, ## $p<0.01$ compared with Normal control: $p<0.05$ (*) & 0.01 (**) compared with Gentamicin (100 mg/kg) i.p

TABLE 12

Individual Animal Histopathological Findings

| Group | Animal No. | Microscopic Findings Kidney | Liver |
|---|---|---|---|
| I | 1 | Tubular dilatation, cortex, minimal Tubular degeneration & regeneration, minimal Inflammatory cells infiltration, BRL Hemorrhages, agonal changes | Inflammatory cells, focal, minimal Congested portal, central vein, and sinusoids agonal changes Increase cytoplasmic glycogen contents |
| | 2 | Tubular dilatation, cortex, minimal Tubular degeneration & regeneration, minimal Congestion, agonal changes Hemorrhages, agonal changes | Cytoplasmic vacuolation, hepatocytes, minimal Increase cytoplasmic glycogen contents Congested portal, central vein, and sinusoids, agonal changes |
| | 3 | Tubular dilatation, cortex, minimal Tubular degeneration & regeneration, minimal Inflammatory cells infiltration, minimal Congestion, agonal changes Hemorrhages, agonal change | Inflammatory cells, multifocal, minimal Increase cytoplasmic glycogen contents Congested portal, central vein, and sinusoids, agonal changes |
| | 4 | Tubular dilatation, cortex, minimal Tubular degeneration & regeneration, minimal Inflammatory cells infiltration, minimal Congestion, agonal changes Hemorrhages, agonal changes | Increase cytoplasmic glycogen contents |
| | 5 and 6 | Tubular dilatation, cortex, minimal Tubular degeneration & regeneration, minimal Congestion, agonal changes Hemorrhages, agonal changes | Increase cytoplasmic glycogen contents Congested portal, central vein, and sinusoids, agonal changes |
| II | 7 | Tubular dilatation, cortex, moderate Inflammatory cells infiltration, multifocal, moderate Tubular degeneration & regeneration with dilatation, multifocal, moderate Tubular cell necrosis, minimal Tubular cell vacuolation, minimal proteineous fluid, minimal, Hemorrhages, agonal changes, Congestion, agonal changes | Increase cytoplasmic glycogen contents Inflammatory cells infiltration, minimal Sinusoidal congestion, agonal change |
| II | 8 | Tubular dilatation, cortex, moderate Inflammatory cells infiltration, multifocal, moderate Tubular degeneration & regeneration with dilatation, multifocal, moderate Tubular cell vacuolation, minimal Proteineous fluid, minimal Congestion, agonal changes | Increase cytoplasmic glycogen contents Inflammatory cells infiltration, minimal Single cell necrosis, minimal |
| | 9 | Tubular dilatation, cortex, moderate Inflammatory cells infiltration, multifocal, moderate Tubular degeneration & regeneration with/without dilatation, multifocal, moderate | Increase cytoplasmic glycogen contents |

TABLE 12-continued

Individual Animal Histopathological Findings

| Group | Animal No. | Microscopic Findings Kidney | Liver |
|---|---|---|---|
| | 10 | Tubular cell vacuolation, minimal proteineous fluid, minimal Congestion, agonal changes Tubular dilatation, cortex, moderate Inflammatory cells infiltration, multifocal, mild Tubular degeneration & regeneration with/without dilatation, multifocal, moderate Tubular cell vacuolation, minimal proteineous fluid, minimal Congestion, agonal changes | Inflammatory cells infiltration, peribilliary mild |
| | 11 | Tubular dilatation, cortex, moderate Inflammatory cells infiltration, mild Tubular degeneration & regeneration with/without dilatation, multifocal, moderate Tubular cell vacuolation, minimal Tubular cell necrosis, minimal | Increase cytoplasmic glycogen contents moderate Sinusoidal congestion, agonal changes |
| II | 12 | Tubular dilatation, cortex, marked Inflammatory cells infiltration, minimal Tubular degeneration & regeneration with/without dilatation, multifocal, moderate Tubular cell vacuolation, minimal Tubular cell necrosis, minimal Inflammatory cells infiltration, glomeruli, minimal | Inflammatory cells infiltration, minimal |
| III | 13 | Tubular dilatation, cortex, mild Inflammatory cells infiltration, multifocal, mild Tubular degeneration & regeneration with/without dilatation, multifocal, mild Congestion, agonal changes Hemorrhages, agonal changes | Sinusoidal congestion, agonal changes |
| | 14 | Tubular dilatation, cortex, mild Inflammatory cells infiltration, multifocal, mild Tubular degeneration & regeneration with/without dilatation, multifocal, mild Congestion, agonal changes Hemorrhages, agonal changes | Inflammatory cells infiltration, minimal Increase cytoplasmic glycogen contents |
| | 15 | Tubular dilatation, cortex, moderate Inflammatory cells infiltration, multifocal, moderate Tubular degeneration & regeneration with/without dilatation, multifocal, moderate Tubular cell vacuolation, minimal Hemorrhages, agonal changes | NAD |
| III | 16 | Tubular dilatation, cortex, moderate Inflammatory cells infiltration, multifocal, moderate Tubular degeneration & regeneration with/without dilatation, multifocal, moderate Tubular cell vacuolation, minimal | Inflammatory cells infiltration, minimal |
| | 17 | Tubular dilatation, cortex, moderate Inflammatory cells infiltration, multifocal, moderate Tubular degeneration & regeneration with/without dilatation, multifocal, moderate Tubular cell vacuolation, minimal, Congestion, agonal changes Hemorrhages, agonal changes | Cytoplasmic vacuolation, hepatocytes, mild Sinusoidal congestion, agonal changes |

TABLE 12-continued

Individual Animal Histopathological Findings

| Group | Animal No. | Microscopic Findings Kidney | Liver |
|---|---|---|---|
|  | 18 | Tubular dilatation, cortex, mild Inflammatory cells infiltration, multifocal, mild Tubular degeneration & regeneration with/without dilatation, multifocal, mild Congestion, agonal changes | Cytoplasmic vacuolation, hepatocytes, minimal |
| IV | 19 | Tubular dilatation, cortex, moderate Inflammatory cells infiltration, multifocal, moderate Tubular degeneration & regeneration with/without dilatation, multifocal, moderate Tubular cell vacuolation, minimal | Inflammatory cells infiltration, minimal Increase cytoplasmic glycogen contents Sinusoidal Congestion, agonal changes |
| IV | 20 | Tubular dilatation, cortex, mild Inflammatory cells infiltration, multifocal, mild Tubular degeneration & regeneration with/without dilatation, multifocal, mild Tubular cell vacuolation, minimal Congestion, agonal changes | Cytoplasmic vacuolation, hepatocytes, minimal Sinusoidal Congestion, agonal changes |
|  | 21 | Tubular dilatation, cortex, minimal Inflammatory cells infiltration, multifocal, mild Tubular degeneration & regeneration with/without dilatation, multifocal, minimal Congestion, agonal changes | NAD |
|  | 22 | Tubular dilatation, cortex, minimal Inflammatory cells infiltration, multifocal, mild Tubular degeneration & regeneration with/without dilatation, multifocal, minimal Congestion, agonal changes | Cytoplasmic vacuolation, hepatocytes, minimal Sinusoidal Congestion, agonal changes |
| IV | 23 | Tubular dilatation, cortex, mild Inflammatory cells infiltration, multifocal, mild Tubular degeneration & regeneration with/without dilatation, multifocal, mild Tubular cell vacuolation, minimal Congestion, agonal changes | NAD |
|  | 24 | Tubular dilatation, cortex, mild Inflammatory cells infiltration, multifocal, mild Tubular degeneration & regeneration with/without dilatation, multifocal, mild Hemorrhages, agonal changes Congestion, agonal changes | Cytoplasmic vacuolation, hepatocytes, minimal Increase cytoplasmic glycogen contents |

TABLE 13

Summary of Grading System for Histopathology Evaluation of Kidney

| Lesions | I/ Normal control/ 6 | II/ Positive control/ 6 | III/ Test drug-low dose (100 mg/kg)/6 | IV/ Test drug-High dose (200 mg/kg)/6 |
|---|---|---|---|---|
| 1. Tubular dilatation, cortex |  6 | 5 | 6 | 6 |
| Minimal | 6 | 0 | 0 | 2 |
| Mild | 0 | 0 | 3 | 3 |

TABLE 13-continued

Summary of Grading System for Histopathology Evaluation of Kidney

| | Group/Treatment/No. of animals | | | |
|---|---|---|---|---|
| Lesions | I/ Normal control/ 6 | II/ Positive control/ 6 | III/ Test drug-low dose (100 mg/kg)/6 | IV/ Test drug-High dose (200 mg/kg)/6 |
| Moderate | 0 | 4 | 3 | 1 |
| Marked | 0 | 1 | 0 | 0 |
| 2. Tubular degeneration and regeneration | 6 | 6 | 6 | 6 |
| Minimal | 6 | 0 | 0 | 2 |
| Mild | 0 | 0 | 3 | 3 |
| Moderate | 0 | 6 | 3 | 1 |
| Marked | 0 | 0 | 0 | 0 |
| 3. Inflammatory cells infiltration, multifocal | 2 | 6 | 6 | 6 |
| Minimal | 2 | 1 | 0 | 0 |
| Mild | 0 | 2 | 3 | 5 |
| Moderate | 0 | 3 | 3 | 1 |
| 4. Inflammatory cells infiltration, glomeruli | 1 | 0 | 0 | 0 |
| Minimal | 1 | 0 | 0 | 0 |
| 5. Tubular cell vacuolation | 0 | 6 | 3 | 3 |
| Minimal | 0 | 6 | 3 | 3 |
| Mild | 0 | 0 | 0 | 0 |
| Moderate | 0 | 0 | 0 | 0 |
| Marked | 0 | 0 | 0 | 0 |
| 6. Proteineous fluid | 0 | 4 | 0 | 0 |
| Minimal | 0 | 4 | 0 | 0 |
| 7. Tubular cell necrosis | 0 | 4 | 0 | 0 |
| Minimal | 0 | 4 | 0 | 0 |
| Mild | 0 | 0 | 0 | 0 |
| Marked | 0 | 0 | 0 | 0 |

TABLE 14

Summary of Grading System for Histopathology Evaluation of Liver

| | Group/Treatment/No. of animals | | | |
|---|---|---|---|---|
| Lesions | I/ Normal control/ 6 | II/ Positive control/ 6 | III/ Test drug-low dose (100 mg/kg)/6 | IV/ Test drug-High dose (200 mg/kg)/6 |
| 1. Inflammatory cells infiltration | 2 | 3 | 2 | 1 |
| Minimal | 2 | 3 | 2 | 1 |
| Mild | 0 | 0 | 0 | 0 |
| 2. Hepatocytes cytoplasmic vacuolation | 1 | 0 | 1 | 2 |
| Minimal | 1 | 0 | 0 | 2 |
| Mild | 0 | 0 | 1 | 0 |
| 3. Single cell necrosis | 0 | 1 | 0 | 0 |
| Minimal | 0 | 1 | 0 | 0 |
| 4. Inflammatory cell infiltration, peribilliary | 0 | 1 | 0 | 0 |
| Mild | 0 | 1 | 0 | 0 |
| 5. Increase cytoplasmic glycogen contents | 4 | 4 | 0 | 1 |

Conclusion:

The results thereby demonstrate that Test drug has potent nephroprotective action upon Gentamycin-induced renal damage in rats and possess antilipid peroxidative and free radical scavenging activities. Further, it demonstrates that treatment with Test drug at 200 mg/kg in rats can prevent functional as well as histological renal changes induced by gentamicin.

Example 2: Clinical Study

Aims and objectives: To prove the efficacy of the Test drug in management of chronic renal failure (CRF). To give the scientific establishment to the observations which show that Test drug significantly correct albuminuria and serum creatinine value, which are the cardinal features of CRF, and improve the renal function which is evident by reduction in serum creatinine and blood urea levels.

Materials and Methods: All the patients were selected from the OPD and IPD of the Muniyal Ayurveda Hospital and Research Centre Manipal.

Criteria for inclusion: Patients with clinically positive history of CRF, having the clinical features of CRF like albuminuria, raised serum creatinine and blood urea, were included.

Criteria for exclusion: The patients having diabetic nephropathy were excluded from this study. Patients who were on dialysis therapy. Patients with other added complications.

Plan of study and management: A total of 100 patients with CRF were registered for the study. The patients were administered with the Test drug tablet, 2 tablets (2×500 mg) twice a day. The patients were kept on normal healthy diet. The doses of the continuous antihypertensive drugs of the patients were not interfered with. Duration of the treatment was 1 month.

Assessment of results: All the patients were clinically assessed before and after treatment. Changes in symptoms, albuminuria, serum creatinine, blood urea and hemoglobin were observed. Observations were evaluated statistically.

Results and Observations: The main causative factor for CRF in this study was hypertension; 86% patients were found in this group. 7% patients were having chronic nephritis and 5% were having polycystic kidney disease. Only 2% of the patients were found with obstructive nephropathy. Serum creatinine reduced by 20.71% and it was statistically highly significant.

Blood urea reduced by 32.15% and it was also statistically highly significant. Albuminuria reduced by 36.70% and this was statistically highly significant. Hemoglobin increased by 4.65% and this was statistically highly significant. None of the patients had shown any new and unusual feature. Urine output increased by 56.54% and it was statistically highly significant. Out of 100 patients, edema was reported by 58 patients and it reduced by 71.56%. Nausea was reported in 46 patients and it was relieved by 68.75%. The 24 patients were found to have vomiting and it was relieved by 82.35%. Weakness was found in 85 patients and it reduced by 55.61%. The 53 patients were having loss of appetite, and appetite increased by 59.29%. Leg cramps were found in 17 patients and it reduced by 72%. Breathlessness was found in 27 patients and it was relieved by 64.29%. Hiccup was found in only one patient and was totally relieved. The 19 patients reported pruritus and it reduced by 66.66%. Reductions in all these symptoms were statistically highly significant.

Discussion and Interpretation: As mentioned earlier, CRF is specific form of renal disease. According to Ayurveda, CRF is a disease of Mutravaha Srotas. Though all the three Doshas as well as all the Dushyas are involved in the disease, Kapha is responsible in blocking micro vessels and developing microangiopathy. Vata is responsible for degeneration of the structure of the kidney. According to Ayurvedic principles of management of the disease, tissue damage can be prevented and repaired by Rasayana drugs because they have the capability to improve qualities of tissues and hence increase resistance of the tissues. On the other hand, blockage can be removed by Lekhana drugs having scraping effect on blocked channels.

In this study, it was found that serum creatinine reduced by 20.71% with treatment. This beneficial effect was statistically highly significant which is encouraging and shows improvement in kidney functions. Blood urea reduced by 36.15% with treatment and it was also statistically highly significant. Treatment resulted in reduction in albuminuria by 36.70% and increase in hemoglobin by 4.65%, which were statistically highly significant. Reduction in edema, weakness, leg cramps, increase in appetite, and relief from nausea, breathlessness and pruritus were statistically highly significant.

Conclusion: With the help of clinical observations and the discussion made, it may be concluded that 86% patients of CRF have hypertension as a basic underlying cause. The result obtained may be attributed to the disease modifying effect of trial therapy by means of its Rasayana and anti Vata-Kapha properties. The trial therapy is an ideal drug as a safe and effective alternative in case of CRF.

Serum creatinine, blood urea and albuminuria reduced 20.71%, 32.15% and 36.70%, respectively. Hemoglobin level and urine output increased by 4.38% and 56.54%, respectively. They were statistically highly significant. All the patients had shown more than 50% relief in all the signs and symptoms.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral formulation for treatment and management of Renal disorders and associated complications, comprising
    *Cinnamomum camphora* in an amount ranging from 1 to 4 wt % of the total formulation; *Acorus calamus* in an amount ranging from 1 to 4 wt % of the total formulation; *Saussurea lappa* in an amount ranging from 1 to 4 wt % of the total formulation; *Andrographis paniculata* in an amount ranging from 1 to 4 wt % of the total formulation; *Tinospora cordifolia* in an amount ranging from 1 to 4 wt % of the total formulation; *Cedrus deodara* in an amount ranging from 1 to 4 wt % of the total formulation; *Curcuma longa* in an amount ranging from 1 to 4 wt % of the total formulation; *Aconitum heterophyllum* in an amount ranging from 1 to 4 wt % of the total formulation; *Berberis aristata* in an amount ranging from 1 to 4 wt % of the total formulation; *Plumbago rosea* in an amount ranging from 1 to 4 wt % of the total formulation; *Coriandrum sativum* in an amount ranging from 1 to 4 wt % of the total formulation; *Emblica officinalis* in an amount ranging from 1 to 4 wt % of the total formulation; *Terminalia chebula* in an amount ranging from 1 to 4 wt % of the total formulation; *Terminalia bellerica* in an amount ranging from 1 to 4 wt % of the total formulation; *Piper chaba* in an amount ranging from 1 to 4 wt % of the total formulation; *Embelia ribes* in an amount ranging from 1 to 4 wt % of the total formulation; *Piper longum* in an amount ranging from 1 to 4 wt % of the total formulation; *Piper nigrum* in an amount ranging from 1 to 4 wt % of the total formulation; *Commiphora mukul* in an amount ranging from 6 to 10 wt % of the total formulation; *Saccharum officinarum* in an amount ranging from 2 to 6 wt % of the total formulation; *Zingiber officinalis* in an amount ranging from 1 to 4 wt % of the total formulation; shilajit in an amount ranging from 6 to 10 wt % of the total formulation; *Operculina turpethum* in an amount less than or equal to 2 wt % of the total formulation; *Baliospermum montanum* in an amount less than or equal to 2 wt % of the total formulation; *Cinnamomum tamala* in an amount less than or equal to 2 wt % of the total formulation; *Cinnamomum zeylanica* in an amount less than or equal to 2 wt % of the total formulation; *Elettaria cardamomum* in an amount less than or equal to 2 wt % of the total formulation; *Bamboo manna* in an amount less than or equal to 2 wt % of the total formulation; *Boerhavia diffusa* in an amount less than or equal to 2 wt % of the total formulation; *Cyperus rotundas* in an amount less than or equal to 2 wt % of the total formulation; *Bauhinia variegata* in an amount less than or equal to 2 wt % of the total formulation; *Holarrhena antidysenterica* in an amount less than or equal to 2 wt % of the total formulation; at least one bhasma; and at least one suitable excipient, wherein said formulation is in the form selected from a group consisting of tablet, capsule and emulsion.

2. The oral formulation as claimed in claim 1, wherein said bhasma is selected from a group consisting of Mandura bhasma and Loha bhasma.

3. The oral formulation as claimed in claim 2, wherein said Mandura Bhasma is present in an amount ranging from 2 to 6 wt % of the total formulation.

4. The oral formulation as claimed in claim 2, wherein said Loha Bhasma is present in an amount ranging from 1 to 4 wt % of the total formulation.

5. The oral formulation as claimed in claim 1, further comprising at least one alkali selected from a group consisting of Yavakshara and Sarjakshara.

6. The oral formulation as claimed in claim 5, wherein each of said alkali is present in an amount less than or equal to 2 wt % of the total formulation.

7. The oral formulation as claimed in claim 1, further comprising at least one salt selected from the group consisting of Rock salt, Sonchal salt and Black salt.

8. The oral formulation as claimed in claim 7, wherein the salt is present in an amount in the range of 1 to 4 wt % of the total formulation.

9. The oral formulation as claimed in claim 1, comprising gum acacia.

10. The oral formulation as claimed in claim 1, further comprising at least one additive selected from a group consisting of flavor, a colorant, a preservative, and a pH adjuster.

* * * * *